US012376767B2

(12) United States Patent
Tscholl et al.

(10) Patent No.: US 12,376,767 B2
(45) Date of Patent: Aug. 5, 2025

(54) COMPUTER SYSTEM AND METHOD FOR BLOOD GAS ANALYSIS SUPPORT

(71) Applicant: Universität Zürich, Zürich (CH)

(72) Inventors: David W. Tscholl, Zürich (CH); Tadzio Raoul Roche, Zürich (CH); Christoph B. Nöthiger, Oberwil-Lieli (CH); Donat R. Spahn, Zürich (CH)

(73) Assignee: Universität Zürich, Zürich (CH)

( * ) Notice: Subject to any disclaimer, the term of this patent is extended or adjusted under 35 U.S.C. 154(b) by 410 days.

(21) Appl. No.: 18/172,053

(22) Filed: Feb. 21, 2023

(65) Prior Publication Data

US 2024/0277261 A1  Aug. 22, 2024

(51) Int. Cl.
*A61B 5/145* (2006.01)
*A61B 5/00* (2006.01)

(52) U.S. Cl.
CPC ............ *A61B 5/145* (2013.01); *A61B 5/0002* (2013.01)

(58) Field of Classification Search
CPC .................................................. A61B 5/145
See application file for complete search history.

*Primary Examiner* — Robert B Mondesi
(74) *Attorney, Agent, or Firm* — Brake Hughes Bellermann LLP

(57) ABSTRACT

Computer system and computer-implemented method for rendering representations of blood gas state parameters of a patient to support a medically trained person in blood gas analysis of the patient's blood, comprising: receiving, from a data source, time series of sampled measurement values obtained from a plurality of blood gas analysis sensors for the following blood gas state parameters of the patient: Glucose, Chloride, Potassium, Calcium, Sodium, and Hemoglobin; mapping each state parameter to a predefined corresponding graphical representation with each graphical representation for a particular state parameter being distinct from all graphical representations of the remaining state parameters; and rendering, in a virtual 3D tunnel shaped scene representing the inside of an artery, animated visualizations of the graphical representations, in accordance with predefined animation rules, such that respective graphical objects move through the inside of the artery and reflect current values of the respective state parameters.

20 Claims, 14 Drawing Sheets

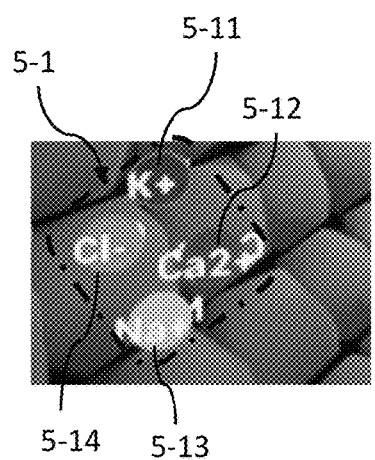
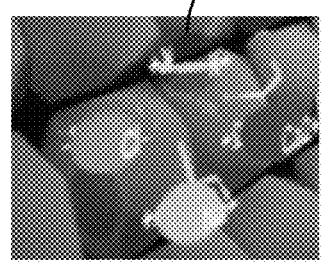
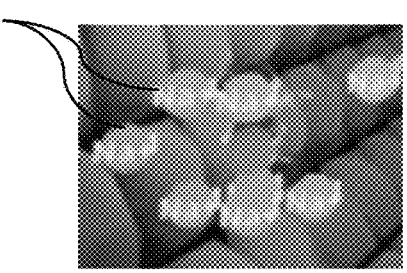
FIG. 5C
FIG. 5A
FIG. 5B
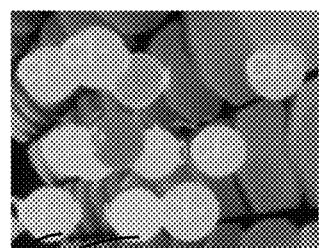
FIG. 5D
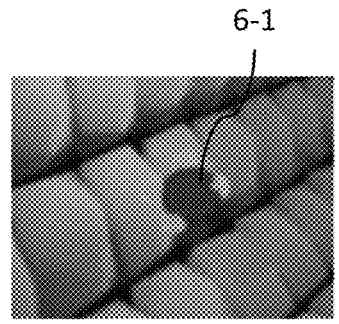
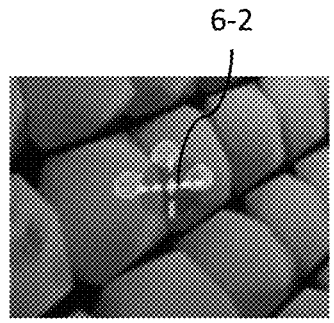
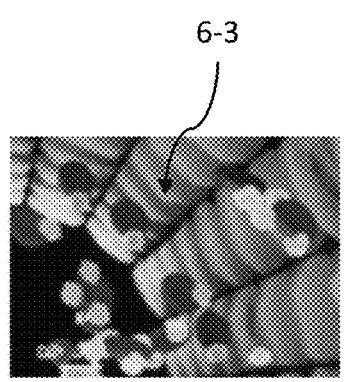
FIG. 6A
FIG. 6B
FIG. 6C

COMPUTER SYSTEM AND METHOD FOR BLOOD GAS ANALYSIS SUPPORT

TECHNICAL FIELD

The present description generally relates to the field of monitoring the clinical state of a patient and, more in particular, relates to an appropriate synthesis of blood test system monitoring information for a user of a blood test monitoring device. Such a user can also be a personal consumer using an e-health app and having an adequate level of medical training. In more detail, the description relates to methods, computer program products and systems for supporting a respectively trained person in blood gas analysis of the blood of a patient, and in particular relates to rendering representations of blood gas state parameters of the patient which are intuitively understood by that person.

BACKGROUND

Blood gas tests are among the most frequently performed diagnostic procedures in modern medicine. They provide valued information about organ dysfunctions, toxic substances in the body, tumor progress, and allow for genetic testing. Such blood test results are typically displayed in numerical values in a hospital information system. Furthermore, blood test function data is being used and displayed in telemedicine products, online and offline hardware and software applications, and a broad scope of consumer health products, e.g., e-health applications for smart devices, for use at home or in retirement homes. A prior art blood test monitoring system may display fifty or more different raw data points on a single screen. However, the number of data points displayed is huge and overwhelms users with information. With a growing number of monitored parameters, it becomes impossible to comprehend all the information consistently and remain aware of the patient's situation (i.e., the patient's medical/clinical state). However, a correct and rapid understanding of a patient's blood test results by the attending medically trained person (e.g., a physician) is vital for patient care. Only when the blood gas diagnostic data is correctly understood, and when there is a high degree of certainty with regard to the understanding, can a physician quickly initiate further diagnostic steps or prescribe the appropriate therapy. Such decisions may need to be taken in real-time to avoid that the patient passes into a critical or even life-threatening state.

SUMMARY

Hence, there is a need for system and method to provide diagnostic tool support to medically trained users which allows such users a quick and intuitive comprehension of the patient's overall medical state with a high level of confidence. This enables such users to quickly arrive at correct diagnoses and apply appropriate therapeutic treatment to the patient if required.

The herein disclosed solution to this information complexity problem is a computer-generated medical instrument, comprising a graphical display, synthesizing raw blood test function data (blood gas state parameters) into a graphical two- or three-dimensional synthetic blood vessel model corresponding to the inside of an artery with relevant blood components, representing the condition of the monitored patient's blood test results according to the raw data input. Compared to a conventional monitoring device, the herein disclosed computer-generated user interface can be read and understood by users with a respective level of medical training much more easily. This can be particularly advantageous when the user must make quick decisions under stress.

With this computer-generated instrument, the relevant information is better perceived by the human visual system and the human neurocognitive system and thus the information is better processed than when users use conventional presentation of laboratory values as provided by prior art tools. This benefit of improved perception through the human visual/neurocognitive systems was demonstrated in a study with 70 participants which is described in detail in the detailed description part of this document. Participating users were more likely to make the correct diagnosis, perceived more laboratory values correctly, and had greater decision-making confidence when they used the herein disclosed computer-generated instrument rather than the corresponding conventional presentation of laboratory results. The computer-generated medical instrument comprises various elements (graphical objects) that interact with each other and intuitively represent the interaction of blood gas state parameters derived from laboratory values and their meaning. By using the graphical animated representations of the patient's blood gas parameters, a human user can retrieve the relevant blood gas state parameter information of the patient directly from such representations and is relieved from mentally translating parameter values (numbers) all the time. In the following, various embodiments of the herein disclosed approach are described. Such embodiments comprise a computer-implemented method, a computer readable medium (computer program product) comprising program instructions that, when loaded into a memory of a computing device and executed by at least one processor of the computing device, cause the at least one processor to execute said method, and a computer system which is adapted to execute said method when executing said computer program.

In a first aspect, a computer-implemented method is provided for rendering representations of blood gas state parameters of a patient to support a medically trained person in blood gas analysis of the patient's blood. The method comprises:

receiving, from a data source, time series of sampled measurement values obtained from a plurality of blood gas analysis sensors for the following blood gas state parameters of the patient: Glucose, Chloride, Potassium, Calcium, Sodium, and Hemoglobin;

mapping each state parameter to a predefined corresponding graphical representation with each graphical representation for a particular state parameter being distinct from all graphical representations of the remaining state parameters; and rendering, in a virtual 3D tunnel shaped scene representing the inside of an artery, animated visualizations of the graphical representations, in accordance with predefined animation rules, such that respective graphical objects move through the inside of the artery to illustrate the blood flow and reflect current values of the respective state parameters.

Thereby, the predefined animation rules comprise:

for the Glucose state parameter:
a non-blinking single Glucose object indicating normal Glucose concentration,
a blinking Glucose object indicating a too low Glucose concentration, and
a cluster of a plurality of non-blinking Glucose objects indicating a too high Glucose concentration;

for electrolyte state parameters Chloride, Potassium, Calcium, and Sodium:
  a two-by-two arrangement of four electrolyte objects with a single non-blinking electrolyte object for each electrolyte indicating normal concentration of the electrolyte parameters,
  the two-by-two arrangement wherein a blinking electrolyte object indicating a too low concentration of the respective electrolyte parameter, and
  the two-by-two arrangement wherein a replication of a particular non-blinking electrolyte object around the two-by-two arrangement, indicating a too high concentration of the respective electrolyte parameter; and for the Hemoglobin state parameter:
  a non-blinking single red blood cell object indicating a normal Hemoglobin value,
  a blinking single red blood cell object indicating a too low Hemoglobin value as an indicator for anemia, and
  a cluster of a plurality of non-blinking red blood cell objects indicating a too high Hemoglobin value.

In one embodiment, all blinking objects may have two alternating states comprising a solid object visualization state and a non-solid object state. A blinking object in the non-solid object state may be outlined with dashed lines. In addition, in the non-solid object state the shape of the object may be indicated by using a semi-transparent color for rendering the object.

In one embodiment, the cluster of the plurality of non-blinking red blood cell objects may be rendered such that the plurality of non-blinking red blood cell objects is placed inside a virtual geometric body with blood cell cluster specific predefined dimensions. For example, a first non-blinking red blood cell object of the cluster may define the center of the blood cell cluster and the remaining non-blinking red blood cell objects of the cluster are rendered around the first non-blinking red blood cell object within a sphere (virtual geometric body) with a predefined red blood cell radius. The virtual geometric body may also be a cube or cuboid with blood cell cluster specific predefined dimensions.

The cluster of the plurality of non-blinking Glucose objects may be rendered such that the plurality of non-blinking Glucose objects is placed inside a virtual geometric body with Glucose cluster specific predefined dimensions. For example, a first non-blinking Glucose object of the Glucose cluster may define the center of the Glucose cluster and the remaining non-blinking Glucose objects of the cluster are rendered around the first non-blinking Glucose object within a sphere (a virtual geometric body) with a predefined Glucose specific radius. As above, other body forms like virtual cube or cuboid bodies with Glucose specific dimensions may be used instead of a sphere.

The replication of the particular non-blinking electrolyte object around the cluster object may be rendered such that the particular non-blinking electrolyte object in the two-by-two arrangement defines the center of a virtual geometric body with predefined electrolyte specific predefined dimensions and one or more replications of the particular non-blinking electrolyte object are rendered within the virtual geometric body with the predefined electrolyte specific dimensions. For example, the particular non-blinking electrolyte object in the two-by-two arrangement may define the center of a sphere with a predefined electrolyte radius and one or more replications of the particular non-blinking electrolyte object are rendered within the sphere with the predefined electrolyte radius. Again, other body forms can be selected.

In one embodiment, the method may further comprise:
  receiving, from the data source, further time series of sampled anion gap state parameter values associated with unspecific anions;
  mapping the anion gap state parameter to a predefined corresponding graphical anion gap representation being distinct from all graphical representations of the remaining state parameters; and
  rendering the anion gap representation in relation to the two-by-two arrangement for the electrolyte state parameters in accordance with predefined anion gap animation rules.

It is to be noted that, because the anion gap representations are associated with a respective two-by-two arrangement, they move through the inside of the artery at the same speed as the two-by-two arrangement. The predefined anion gap animation rules comprise:
  the two-by-two arrangement for the electrolyte state parameters being orbited by an unspecific anion object, indicating a normal anion gap, with the center of the orbit located at the center of the two-by-two arrangement, and a radius of the orbit being greater than a predefined electrolyte radius used for rendering replications of a particular non-blinking electrolyte object around the two-by-two arrangement,
  the two-by-two arrangement for the electrolyte state parameters being orbited with said radius of the orbit by a plurality of unspecific anion objects, indicating a too high anion gap, and
  the two-by-two arrangement for the electrolyte state parameters being orbited by a single blinking unspecific anion object, indicating a too low anion gap.

In one embodiment, the method may further comprise:
  receiving, from the data source, further time series of sampled measurement values for an oxygen affinity state parameter of the patient;
  mapping the oxygen affinity state parameter to a predefined corresponding graphical oxygen affinity representation being distinct from all graphical representations of the remaining state parameters; and
  rendering the oxygen affinity representation in relation to the red blood cell object, with a plurality of bound oxygen objects attached to the red blood cell object, in accordance with predefined oxygen affinity animation rules, comprising:

It is to be noted that the bound oxygen objects move through the inside of the artery at the same speed as their associated red blood cell object. The predefined oxygen affinity animation rules comprise:
  one oxygen object being released by the red blood cell object in the course of moving through the artery indicating normal oxygen affinity,
  all oxygen objects being released by a red blood cell object in the course of moving through the artery indicating too low oxygen affinity, and
  all oxygen objects with a rubber band animation oscillating between their neutral positions and a position at a predefined oscillation distance from the red blood cell surface, in the course of moving through the artery, indicating too high oxygen affinity.

In one embodiment, method further comprises:
  receiving, from the data source, further time series of sampled measurement values for an oxygen saturation state parameter of the patient;

mapping the oxygen saturation state parameter to a predefined corresponding graphical oxygen saturation representation being distinct from all graphical representations of the remaining state parameters; and
rendering the oxygen saturation representation in accordance with predefined oxygen saturation animation rules.

The predefined oxygen saturation animation rules comprise:
a non-blinking single red blood cell object loaded with a plurality of bound oxygen objects, indicating a normal oxygen saturation, and
a non-blinking single red blood cell object having an alert color with a single bound oxygen object, indicating a too low oxygen saturation.

In one embodiment, the method further comprises:
receiving, from the data source, further time series of sampled measurement values for a Methemoglobin state parameter of the patient;
mapping the Methemoglobin state parameter to a predefined corresponding graphical Methemoglobin representation being distinct from all graphical representations of the remaining state parameters; and
rendering the Methemoglobin representation in accordance with predefined Methemoglobin animation rules.

The predefined Methemoglobin animation rules comprise:
the non-blinking single red blood cell object loaded with a plurality of bound oxygen objects, indicating a normal Methemoglobin level, and
the non-blinking single red blood cell object having the alert color with a single bound oxygen object and, in addition, a plurality of Methemoglobin level labels, indicating a too high Methemoglobin level with limited oxygen transport capacity.

In one embodiment, the method further comprises:
receiving, from the data source, further time series of sampled measurement values for a Carbonmonoxy state parameter of the patient;
mapping the Carbonmonoxy state parameter to a predefined corresponding graphical Carbonmonoxy representation being distinct from all graphical representations of the remaining state parameters; and
rendering the Carbonmonoxy representation in accordance with predefined Carbonmonoxy animation rules.

The predefined Carbonmonoxy animation rules comprise:
a non-blinking single red blood cell object loaded with a plurality of bound oxygen objects, indicating a normal Carbonmonoxy level, and
a single red blood cell object having an alert color with a plurality of bound carbonmonoxy objects instead of the bound oxygen objects, and with the red blood cell leaving behind a trail of fire in the course of moving through the artery, indicating a too high Carbonmonoxy level.

In one embodiment, the method further comprises:
receiving, from the data source, further time series of sampled measurement values for an Oxygen Partial Pressure (OPP) state parameter of the patient;
mapping the OPP state parameter to a predefined corresponding graphical OPP representation being distinct from all graphical representations of the remaining state parameters; and
rendering the OPP representation in accordance with predefined OPP animation rules.

The predefined OPP animation rules comprise:
a non-blinking single red blood cell object indicating a normal OPP level,
a non-blinking single red blood cell object surrounded by a cluster with at least a predefined high-OPP-level-number of unbound non-blinking oxygen objects, indicating a high OPP level, and
a non-blinking single red blood cell object surrounded by a cluster with at most a predefined low-OPP-level-number of unbound blinking oxygen objects, indicating a low OPP level.

In one embodiment, the method further comprises:
receiving, from the data source, further time series of sampled measurement values for a CO2 partial pressure state parameter of the patient;
mapping the CO2 partial pressure state parameter to a predefined corresponding graphical CO2 partial pressure representation being distinct from all graphical representations of the remaining state parameters; and
rendering the CO2 partial pressure representation in accordance with predefined CO2 partial pressure animation rules such that respective graphical CO2 objects move through the inside of the artery and reflect current values of the CO2 partial pressure state parameter.

The predefined CO2 partial pressure animation rules comprise:
a non-blinking single CO2 object indicating a normal CO2 partial pressure,
a blinking single CO2 object indicating a too low CO2 partial pressure, and
a cluster of a plurality of non-blinking CO2 objects indicating a too high CO2 partial pressure.

In one embodiment, the method further comprises:
receiving, from the data source, further time series of sampled measurement values for a Plasma Osmolarity parameter of the patient,
mapping the Plasma Osmolarity state parameter to a predefined corresponding graphical Plasma Osmolarity representation being distinct from all graphical representations of the remaining state parameters; and
rendering, in the virtual 3D tunnel shaped scene representing the inside of the artery, animated visualizations of graphical Plasma Osmolarity representations, in accordance with predefined Plasma Osmolarity animation rules.

The predefined Plasma Osmolarity animation rules comprise:
a plurality of droplet objects diffusing in and out through the blood vessel wall of the artery indicating normal Plasma Osmolarity, wherein each droplet object has a shape indicating the diffusion direction of the respective droplet object,
a plurality of droplet objects only diffusing into the artery through the blood vessel wall, indicating a too low Plasma Osmolarity, and
a plurality of droplet objects only diffusing out of the artery through the blood vessel wall, indicating a too high Plasma Osmolarity.

In one embodiment, the method further comprises:
receiving, from the data source, further time series of sampled measurement values for Acid-Base Balance state parameters of the patient, comprising pH level, bicarbonate concentration, base excess level, lactate concentration,
mapping each Acid-Base Balance state parameter to a predefined corresponding graphical Acid-Base Balance representation being distinct from all graphical representations of the remaining state parameters; and rendering, in the virtual 3D tunnel shaped scene representing the inside of the artery, animated visualizations of the graphical Acid-Base Balance representations by using an animated balance object placed at a fixed location at the bottom of the artery, in accordance with predefined Acid-Base Balance animation rules.

It is to be noted that all animation objects which are associated with the animated balance object, do not flow through the internal of the artery. The Acid-Base Balance animation rules comprise:

for the pH level state parameter:
  a non-blinking single H+ object associated with an acid weighing pan of the balance object, and a non-blinking unspecific base object associated with a base weighing pan of the balance object, with both weighing pans being balanced, indicating a normal pH level,
  a cluster of a plurality of non-blinking H+ objects associated with the acid weighing pan wherein the acid weighing pan is down, indicating a too low pH level, and
  a blinking $H^+$ object associated with the acid weighing pan wherein the base weighing pan is down, indicating a too high pH level with alkaline components predominating;

for the base excess level state parameter:
  a cluster of a plurality of non-blinking unspecific base objects associated with the base weighing pan continuously releasing soap bubbles indicating too high base excess, and
  a blinking single unspecific base object associated with the base weighing pan indicating too low base excess;

for the lactate concentration state parameter:
  a cluster of a plurality of non-blinking milk bottle objects associated with the acid weighing pan, indicating a too high value of lactate concentration, and
  any other balance representation indicating a normal lactate concentration;

for the bicarbonate concentration state parameter:
  a non-blinking single HCO3- object associated with the base weighing pan, indicating normal bicarbonate concentration,
  a blinking single HCO3- object associated with the base weighing pan indicating too low bicarbonate concentration, and
  a cluster of a plurality of non-blinking s HCO3- objects associated with the base weighing pan, indicating a too high bicarbonate concentration.

In a second aspect, a computer readable medium (computer program product) is provided comprising program instructions that, when loaded into a memory of a computing device and executed by at least one processor of the computing device, cause the at least one processor to execute the steps for rendering representations of blood gas state parameters of a patient to support a medically trained person in blood gas analysis of the patient's blood. The computer program can have instructions which implement any rendering step as described for the computer-implemented method. The computer program product includes at least instructions for:

receiving, from a data source, time series of sampled measurement values obtained from a plurality of blood gas analysis sensors for the following blood gas state parameters of the patient: Glucose, Chloride, Potassium, Calcium, Sodium, and Hemoglobin;

mapping each state parameter to a predefined corresponding graphical representation with each graphical representation for a particular state parameter being distinct from all graphical representations of the remaining state parameters; and rendering, in a virtual 3D tunnel shaped scene representing the inside of an artery, animated visualizations of the graphical representations, in accordance with predefined animation rules, such that respective graphical objects move through the inside of the artery and reflect current values of the respective state parameters.

The predefined animation rules comprise:

for the Glucose state parameter:
  a non-blinking single Glucose object indicating normal Glucose concentration,
  a blinking Glucose object indicating a too low Glucose concentration, and
  a cluster of a plurality of non-blinking Glucose objects indicating a too high Glucose concentration;

for electrolyte state parameters Chloride, Potassium, Calcium, and Sodium:
  a two-by-two arrangement of four electrolyte objects with a single non-blinking electrolyte object for each electrolyte indicating normal concentration of the electrolyte parameters,
  the two-by-two arrangement wherein a blinking electrolyte object, indicating a too low concentration of the respective electrolyte parameter, and
  the two-by-two arrangement wherein a replication of a particular non-blinking electrolyte object around the two-by-two arrangement, indicating a too high concentration of the respective electrolyte parameter; and for the Hemoglobin state parameter:
  a non-blinking single red blood cell object indicating a normal Hemoglobin value,
  a blinking single red blood cell object indicating a too low Hemoglobin value as an indicator for anemia, and
  a cluster of a plurality of non-blinking red blood cell objects indicating a too high Hemoglobin value.

The computer program product may be configured such that all blinking objects have two alternating states comprising a solid object visualization state and a non-solid object state, a blinking object in the non-solid object state being outlined with dashed lines. Optionally, in in the non-solid object state, the shape of the blinking object may be rendered using a semi-transparent color.

In one embodiment, the computer program product may be configured such that:

the cluster of the plurality of non-blinking red blood cell objects is rendered such that the plurality of non-blinking red blood cell objects is placed inside a virtual geometric body with predefined blood cell cluster specific dimensions;

the cluster of the plurality of non-blinking Glucose objects is rendered such that the plurality of non-blinking Glucose objects is placed inside a virtual geometric body with predefined Glucose cluster specific dimensions; and the replication of the particular non-blinking electrolyte object around the two-by-two arrangement is rendered such that the particular non-blinking electrolyte object in the two-by-two arrangement defines the center of a virtual geometric body with predefined electrolyte specific dimensions and one or more replications of the particular non-blinking electrolyte object are rendered within the virtual geometric body with the predefined electrolyte specific dimensions.

In a third aspect, a computer system is provided for rendering representations of medical state parameters of a patient to support a medically trained person in blood gas analysis of the blood of the patient, comprising:
- an interface adapted to receive, from a data source, time series of sampled measurement values obtained from a plurality of blood gas analysis sensors for the following blood gas state parameters of the patient: Glucose, Chloride, Potassium, Calcium, Sodium, and Hemoglobin;
- a mapper module adapted to map each state parameter to a predefined corresponding graphical representation with each graphical representation for a particular state parameter being distinct from all graphical representations of the remaining state parameters; and
- a renderer module adapted to render, in a virtual 3D tunnel shaped scene representing the inside of an artery, animated visualizations of the graphical representations, in accordance with predefined animation rules, such that respective graphical objects move through the inside of the artery and reflect current values of the respective state parameters.

The predefined animation rules comprise:
for the Glucose state parameter:
- a non-blinking single Glucose object indicating normal Glucose concentration,
- a blinking Glucose object indicating a too low Glucose concentration, and
- a cluster of a plurality of non-blinking Glucose objects indicating a too high Glucose concentration;

for electrolyte state parameters Chloride, Potassium, Calcium, and Sodium:
- a two-by-two arrangement of four electrolyte objects with a single non-blinking electrolyte object for each electrolyte indicating normal concentration of the electrolyte parameters,
- the two-by-two arrangement wherein a blinking electrolyte object indicating a too low concentration of the respective electrolyte parameter, and
- the two-by-two arrangement wherein a replication of a particular non-blinking electrolyte object around the two-by-two arrangement, indicating a too high concentration of the respective electrolyte parameter; and for the Hemoglobin state parameter:
- a non-blinking single red blood cell object indicating a normal Hemoglobin value,
- a blinking single red blood cell object indicating a too low Hemoglobin value as an indicator for anemia, and
- a cluster of a plurality of non-blinking red blood cell objects indicating a too high Hemoglobin value.

In one embodiment, the computer system is configured adapted such that all blinking objects have two alternating states comprising a solid object visualization state and a non-solid object state, a blinking object in the non-solid object state being outlined with dashed lines. Optionally, in in the non-solid object state, the shape of the blinking object may be rendered using a semi-transparent color.

In one embodiment the computer system is further adapted such that:
the cluster of the plurality of non-blinking red blood cell objects is rendered such that the plurality of non-blinking red blood cell objects is placed inside a virtual geometric body with predefined blood cell cluster specific dimensions;
the cluster of the plurality of non-blinking Glucose objects is rendered such that the plurality of non-blinking Glucose objects is placed inside a virtual geometric body with predefined Glucose cluster specific dimensions; and
the replication of the particular non-blinking electrolyte object around the two-by-two arrangement is rendered such that the particular non-blinking electrolyte object in the two-by-two arrangement defines the center of a virtual geometric body with predefined electrolyte specific dimensions and one or more replications of the particular non-blinking electrolyte object are rendered within the virtual geometric body with the predefined electrolyte specific dimensions.

In one embodiment, the system is further adapted in that:
the interface is further adapted to receive, from the data source, further time series of sampled measurement values for a Plasma Osmolarity parameter of the patient,
the mapper module is further adapted to map the Plasma Osmolarity state parameter to a predefined corresponding graphical Plasma Osmolarity representation being distinct from all graphical representations of the remaining state parameters; and
the renderer module is further adapted to render, in the virtual 3D tunnel shaped scene representing the inside of the artery, animated visualizations of graphical Plasma Osmolarity representations, in accordance with predefined Plasma Osmolarity animation rules.

The predefined Plasma Osmolarity animation rules comprise:
- a plurality of droplet objects diffusing in and out through the blood vessel wall of the artery indicating normal Plasma Osmolarity, wherein each droplet object has a shape indicating the diffusion direction of the respective droplet object,
- a plurality of droplet objects only diffusing into the artery through the blood vessel wall, indicating a too low Plasma Osmolarity, and
- a plurality of droplet objects only diffusing out of the artery through the blood vessel wall, indicating a too high Plasma Osmolarity.

In one embodiment, the system is further adapted in that:
the interface is further adapted to receive, from the data source, further time series of sampled measurement values for Acid-Base Balance state parameters of the patient, comprising pH level, bicarbonate concentration, base excess level, lactate concentration,
the mapper module is further adapted to map each Acid-Base Balance state parameter to a predefined corresponding graphical Acid-Base Balance representation being distinct from all graphical representations of the remaining state parameters; and
the renderer module is further adapted to render, in the virtual 3D tunnel shaped scene representing the inside of the artery, animated visualizations of the graphical Acid-Base Balance representations by using an animated balance object placed at a fixed location at the bottom of the artery, in accordance with predefined Acid-Base Balance animation rules.

The Acid-Base Balance animation rules comprise:
for the pH level state parameter:
a non-blinking single H+ object associated with an acid weighing pan of the balance object, and a non-blinking unspecific base object associated with a base weighing pan of the balance object, with both weighing pans being balanced, indicating a normal pH level, a cluster of a plurality of non-blinking H+ objects associated with the acid weighing pan wherein the acid weighing pan is down, indicating a too low pH level, and a blinking H$^+$ object associated with the acid weighing pan wherein the base weighing pan is down, indicating a too high pH level with alkaline components predominating;

for the base excess level state parameter:
a cluster of a plurality of non-blinking unspecific base objects associated with the base weighing pan continuously releasing soap bubbles indicating too high base excess, and a blinking single unspecific base object associated with the base weighing pan indicating too low base excess;

for the lactate concentration state parameter:
a cluster of a plurality of non-blinking milk bottle objects associated with the acid weighing pan, indicating a too high value of lactate concentration, and any other balance representation indicating a normal lactate concentration;

for the bicarbonate concentration state parameter:
a non-blinking single HCO3- object associated with the base weighing pan, indicating normal bicarbonate concentration, a blinking single HCO3- object associated with the base weighing pan indicating too low bicarbonate concentration, and a cluster of a plurality of non-blinking single HCO3- object associated with the base weighing pan, indicating a too high bicarbonate concentration.

Further aspects of the description will be realized and attained by means of the elements and combinations particularly depicted in the appended claims. It is to be understood that both, the foregoing general description and the following detailed description are exemplary and explanatory only and are not restrictive.

BRIEF DESCRIPTION OF THE DRAWINGS

FIGS. 5A to 5D illustrate example rendering results of electrolyte objects for electrolyte state parameters in accordance with three respective predefined animation rules according to an embodiment;

FIGS. 6A to 6C illustrate example rendering results of red blood cell objects for a Hemoglobin state parameter in accordance with three respective predefined animation rules according to an embodiment;

DETAILED DESCRIPTION

Figure 1:
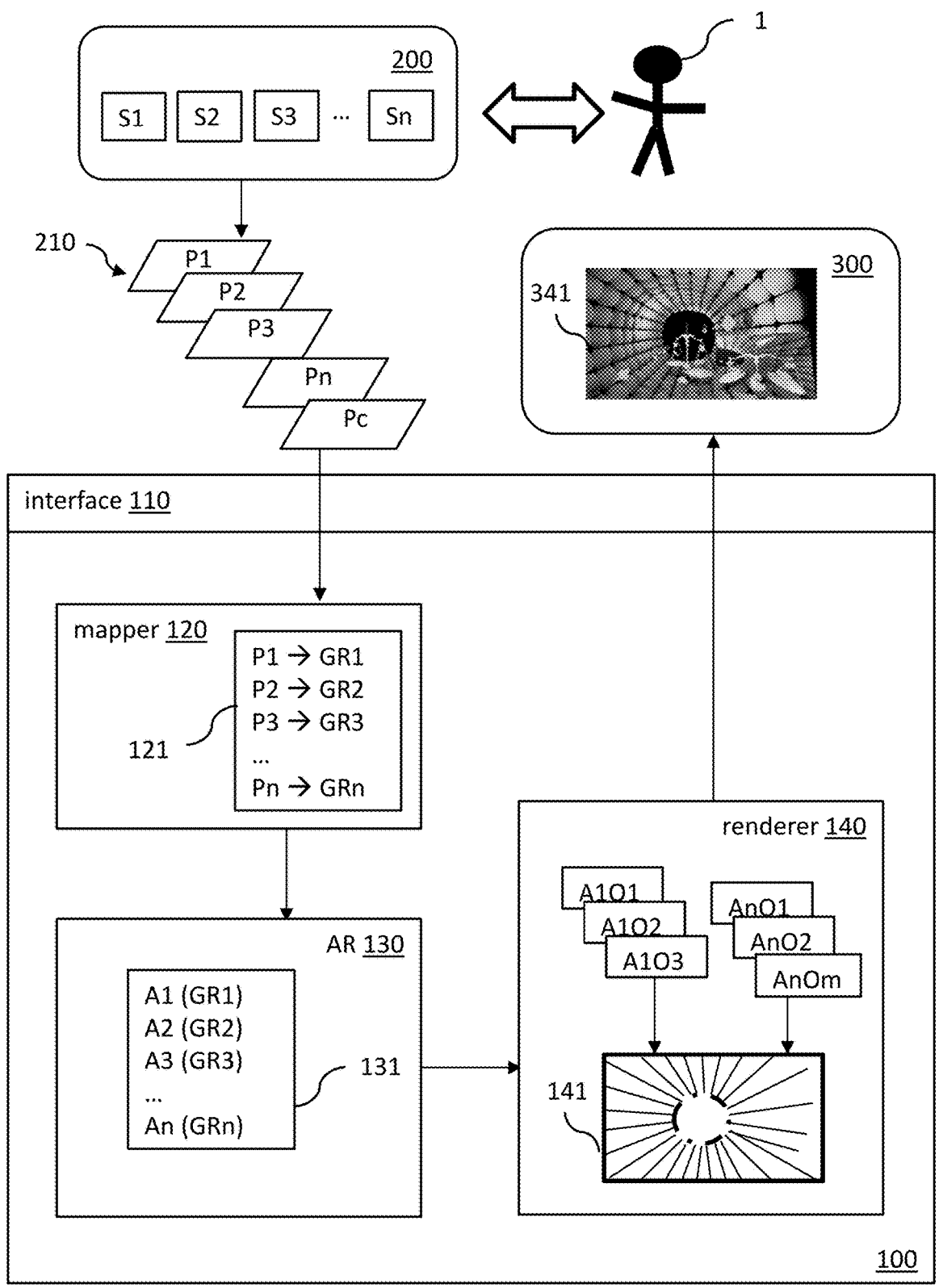
FIG. 1 shows a simplified diagram of a computer system for rendering representations of blood gas state parameters of a patient according to an embodiment.
Figure 2A:
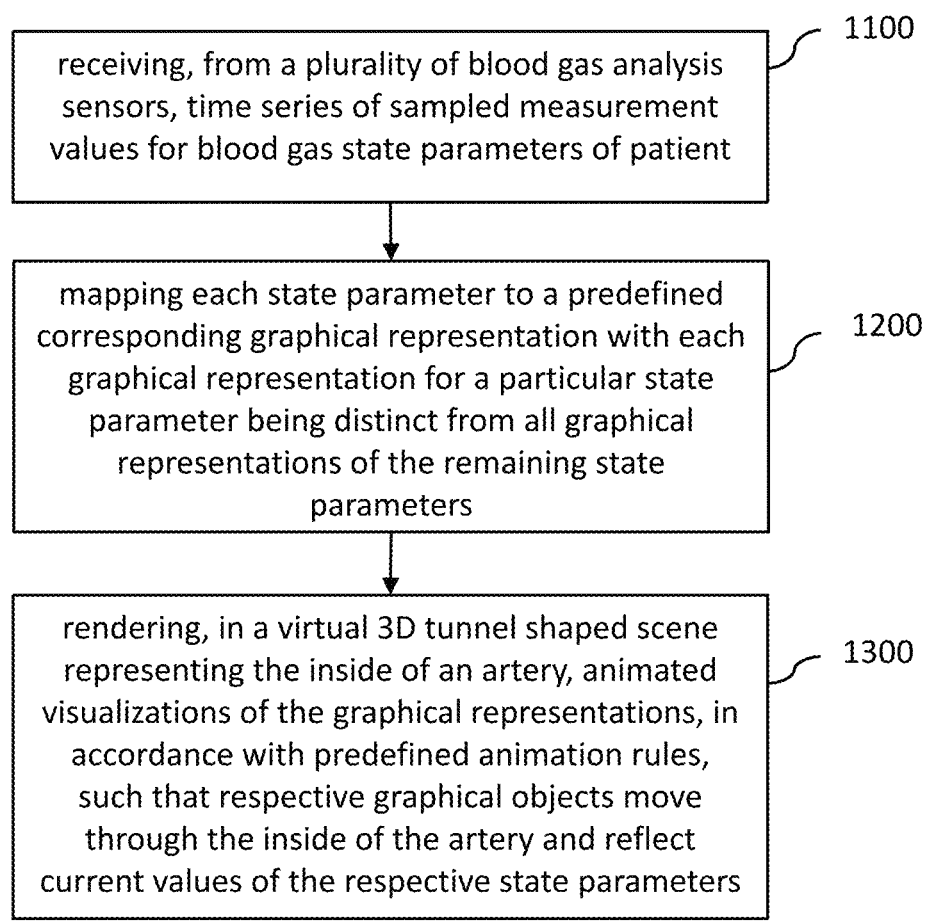
FIG. 2A is a simplified flowchart of a computer-implemented method for rendering representations of blood gas state parameters of a patient according to an embodiment.
Figure 2B:
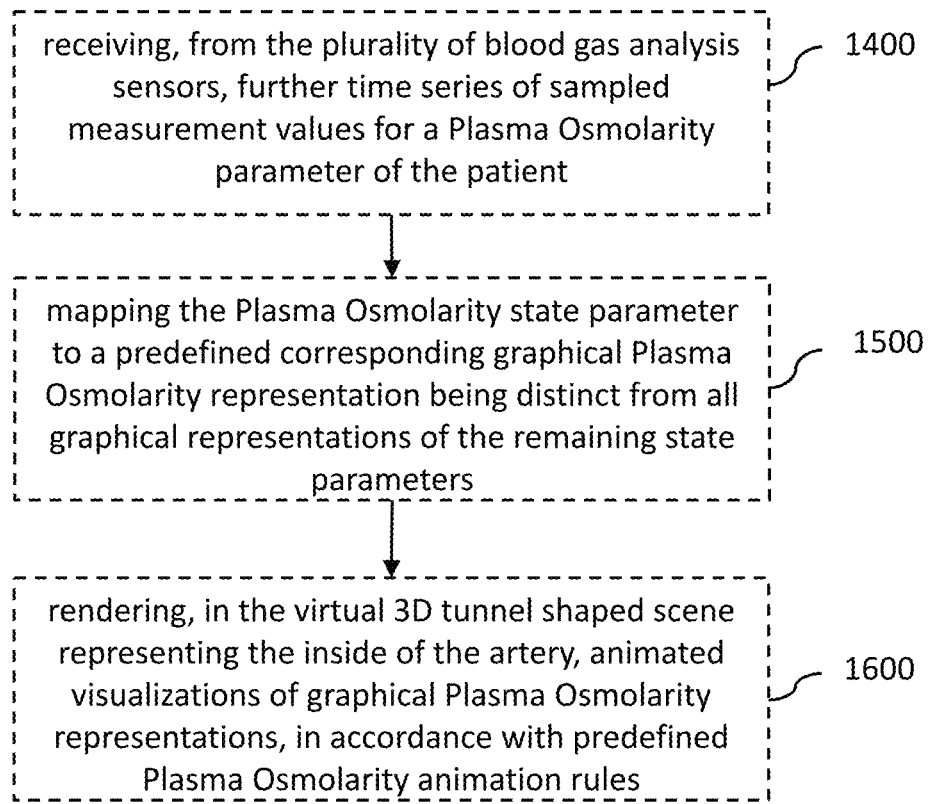
FIGS. 2B, 2C are simplified flowcharts illustrating optional steps in optional embodiments of said computer-implemented method.
Figure 2C:
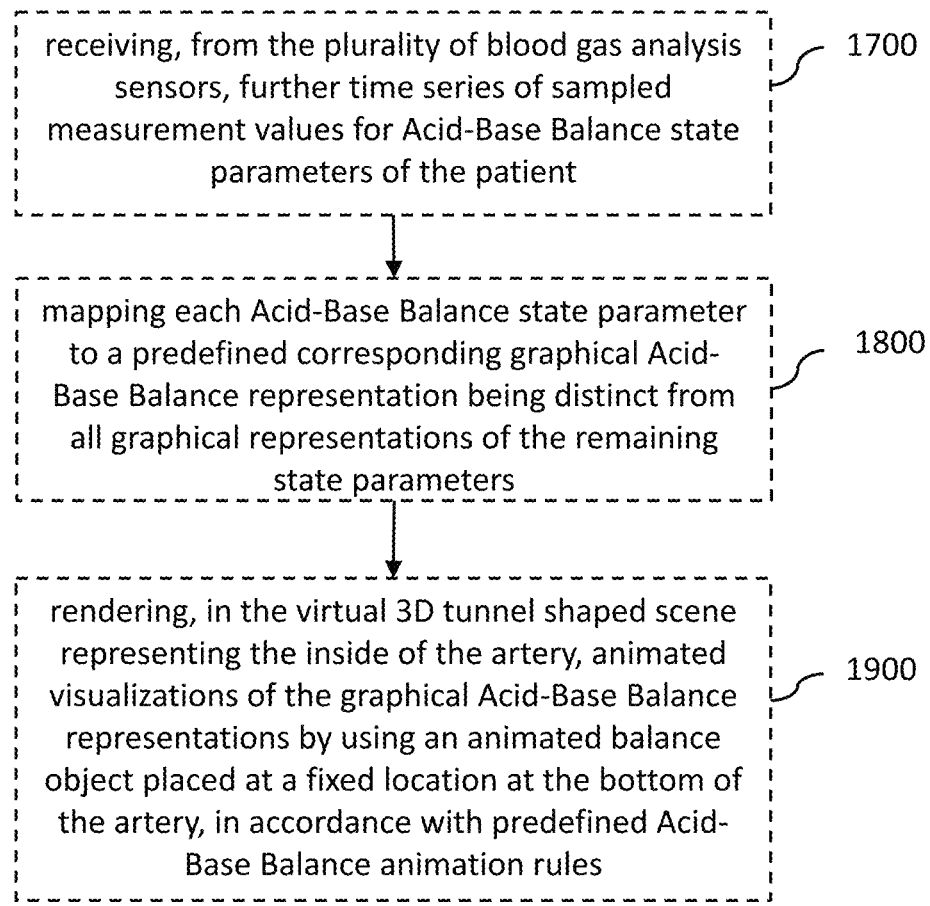

FIG. 1 shows a simplified diagram of an embodiment of a computer system 100 for rendering representations of blood gas state parameters P1 to Pn, Pc of a patient 1 to support a medically trained person in blood gas analysis of the blood of said patient 1. FIG. 2A is a simplified flowchart of a computer-implemented method 1000 for rendering representations of such medical state parameters of the patient 1 to support a medically trained person in blood gas analysis of the blood of the patient. The method 1000 can be performed by system 100. The following description describes the system 100 in the context of method 1000 and, therefore, refers to reference numbers of FIG. 1 and FIG. 2A.

The system 100 is communicatively coupled with a data source 200 which provides blood gas state parameter values 210 of patient 1 which have been obtained either directly by respective blood gas sensors S1 to Sn, or which may be computed based on respective sensor raw data. For example, the hemoglobin value of the patient is a blood gas state parameter (e.g., P1) which is directly obtained by a respective sensor. On the other hand, the anion gap of the patient is a blood gas parameter (e.g., Pc) which is computed based on other directly measured blood gas parameters. Typically, also computed blood gas parameters are provided by the data source 200. The data source may include the respective sensors S1 to Sn and implement the necessary algorithm(s) to provide the measured and computed blood gas state parameters 210 substantially in real time to system 100 while the patient 1 is being monitored by the blood gas sensors S1 to Sn. However, the blood gas parameters 210 may also be buffered by the data source 200 or even be stored in an intermediate storage device (not shown), and then be retrieved from the buffer or storage device by system 100 via an appropriate interface 110. The interface 110 may be any standard interface which is appropriate for the exchange of data.

The system 100 receives 1100 (via interface 110) from the data source, time series of sampled measurement values for blood gas state parameters of the patient 1. In a basic embodiment, the received time series include values for the blood gas parameters Glucose, Chloride, Potassium, Calcium, Sodium, and Hemoglobin. This combination of blood gas parameters typically allows a medically trained person to assess the patient's medical condition already with a high level of accuracy.

The received blood gas state parameter values 210 are then further processed by a mapper 120 module of system 100. The mapper 120 implements a mapping algorithm which maps 1200 each state parameter to a predefined corresponding graphical representation. For example, the Hemoglobin parameter may be mapped to graphic object which has the shape of a red blood cell. Of course, other graphical representations may be used. However, it is advantageous to use a graphical representation for a particular state parameter which is somehow associated with the respective state parameter. Another example can be the use of a sugar cube shaped graphic object as a graphical representation of the Glucose parameter. In any case, each graphical representation for a particular state parameter is distinct from all graphical representations of the remaining state parameters. Advantageously, similarities between distinct graphical representations are avoided to ensure that the human visual system is able to distinguish the distinct graphical representations without a need for the human brain to perform complex mapping activities in the medically trained user's mental model which maps the graphical representations to the associated blood gas state parameters.

In the example embodiment of FIG. 1, the mapper 120 uses mapping rules 121 to map the state parameter P1 to a first graphical representation GR1, P2 to a second, distinct graphical representation GR2, P3 to a third, distinct graphical representation GR3 and so on until the last state parameter Pn is mapped to distinct graphical representation GRn. For the mapped graphical representations, the system has a set of predefined animation rules 131. The animation rules 131 are provided by an animation rule module AR 130. Thereby, for each graphical representation a subset of animation rules defines how the respective graphical object is to be rendered with animations that reflect the current value of the respective blood gas state parameter. For example, subset A1 includes one or more animation rules for the graphical representation GR1. Subset A2 includes one or more animation rules for the graphical representation GR2. Subset A3 includes one or more animation rules for the graphical representation GR3, and so on. Finally, subset An includes one or more animation rules for the graphical representation GRn. A subset of animation rules for a particular blood gas state parameter may, for example, include a first animation rule which reflects a normal state parameter value, a second animation rule which reflects a too high state parameter value, and a third animation rule which reflects a too low state parameter value. Some state parameters may be associated with only two states (e.g., normal, abnormal) in which case only two corresponding animation rules may be included in the respective subset. On the other hand, more than three states for a blood gas state parameter (e.g., critical high, too high, normal, too low, critical low) may also be supported in which case a corresponding animation rule for each state can be included in the respective subset.

In the example of the embodiment according to FIG. 1, the AR 130 module and the mapper 120 are integrated modules of system 100. However, these modules can also be provided by a remote device on a remote storage which is accessible by system 100 to retrieve the mapping 121 as well as the predefined animation rules 131 from the remote device.

A renderer 140 module of system 100 finally renders 1300 animated visualizations of the graphical representations in a virtual 3D tunnel shaped scene 141 representing the inside of an artery. The animated visualizations of the graphical representations are generated in accordance with the predefined animation rules, such that respective graphical objects A1O1, A1O2, A1O3, ..., AnO1, AnO2, AnOm move through the inside of the artery and reflect current values of the respective state parameters. Thereby, the graphical objects A1O1, A1O2, A1O3 represent three different animations as generated by the subset A1 of the predefined animation rules 131. The final rendering result 341 is then visualized on a display device 300 to the medically trained user (not shown). Of course, the result may also be displayed to the patient 1 in case the patient is in a condition which allows to look at the result. However, as shown in the description of the study below, in particular medically trained users benefit from the herein disclosed rendering result 341.

Figure 3:
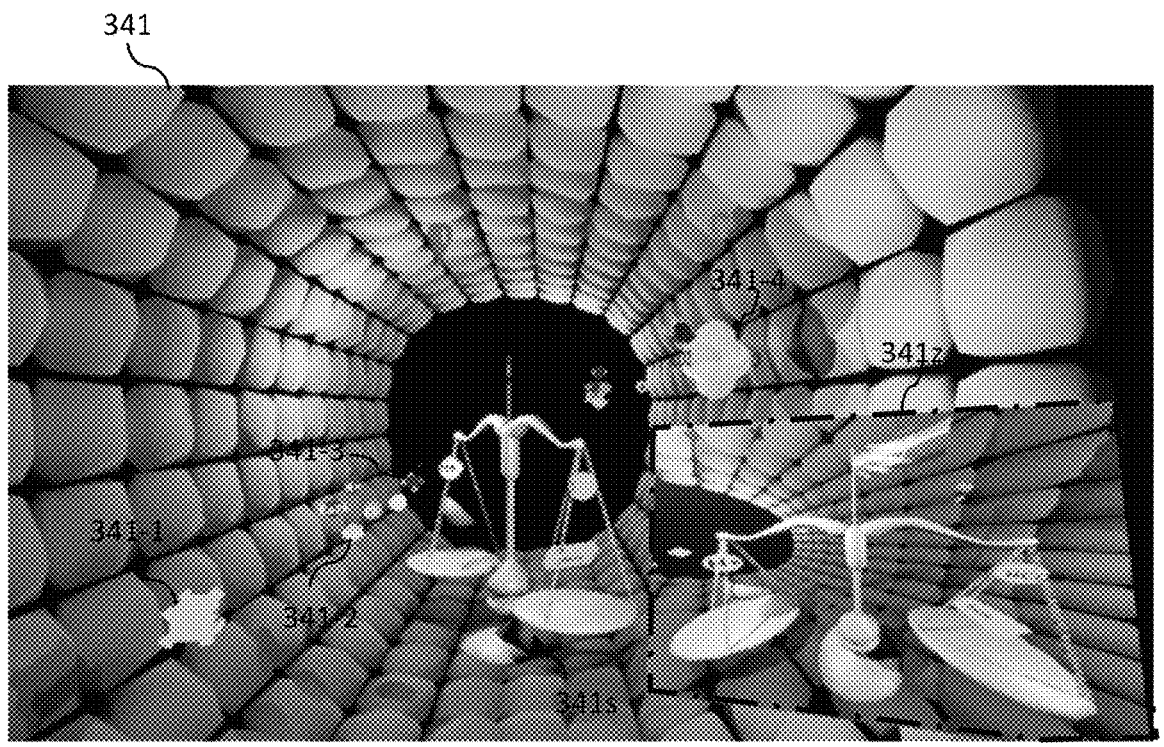
FIG. 3 illustrates a virtual 3D tunnel shaped scene representing the inside of an artery as rendered in accordance with an embodiment.

Turning briefly to FIG. 3, an example of a rendering result 341 taken from an optional embodiment used in said study illustrates different animated graphical objects 341-1 to 342-4 with each graphical object being a graphical representation of another blood gas state parameter. The graphical objects 341-1 to 342-4 all move at the same speed through the inside of the artery. In the study, the flow direction was from the back of the tunnel to the front. However, the flow direction may also be from front to back. In the lower right corner of the rendering result 341, a zoom view 341z (illustrated by a dash-dotted frame) of the graphical object 341s is shown. Graphical object 341s represents a balance object which is part of an optional embodiment to visualize further blood gas state parameters which are associated with said balance and which do not move through the tunnel scene but which are animated at the location where the balance object 341s is located.

The predefined animation rules of the basic embodiment are now described in more detail by referring to FIGS. 4,*

5*, and 6*. The animation rules described with reference to FIGS. 7* to 13* are all considered to be optional embodiments.

In the basic embodiment, the following predefined animation rules may be used for animating the graphical representations of the Glucose, Chloride, Potassium, Calcium, Sodium, and Hemoglobin state parameters.

Figure 4A:
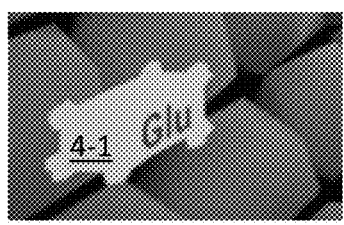
FIGS. 4A to 4C illustrate example rendering results of Glucose objects for a Glucose state parameter in accordance with three respective predefined animation rules according to an embodiment.
Figure 4B:
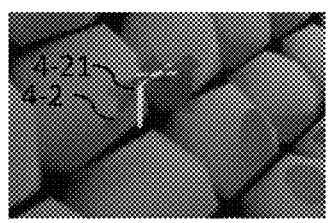
Figure 4C:
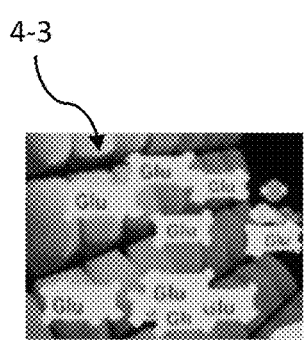

FIGS. 4A to 4C—Animation Rule Subset for the Glucose State Parameter

FIG. 4A illustrates a first animation rule example of the Glucose animation rule subset for rendering a non-blinking single Glucose object 4-1 indicating normal Glucose concentration. In the example, Glucose object 4-1 is shaped like a sugar cube and carries a label 'Glu' which facilitates the association with the Glucose state parameter. Other graphic objects, such as for example a sugar sack shaped object, may be selected as representation of the Glucose state parameter. However, independent of the object shape and labeling, the object is permanently visible (non-blinking) while moving through the inside of the artery.

In general, multiple single graphic objects of a given object type may move through the artery simultaneously. For example, a first object may move along the lower left side of the vessel and a second object of the same object type may move along the upper right side. A new object of the same type may appear at the back of the tunnel when a current object disappears from the view at the front of the tunnel. Two objects of the same type may be rendered at different distances from the back of the tunnel.

FIG. 4B illustrates a second animation rule example of the Glucose animation rule subset for rendering a blinking Glucose object 4-2, indicating a too low Glucose concentration.

In general, A too low blood gas state parameter value (e.g., too low Glucose concentration) can be determined by comparing the measured state parameter with a respective predefined low-level threshold.

In general, blinking objects have two alternating states comprising a solid object visualization state and a non-solid object state. The solid object visualization state of the Glucose object corresponds to the visualization state described in FIG. 4A. In the non-solid object state, the Glucose object may become invisible. That is, when the Glucose object switches back to the solid object visualization state it has moved to a new location. To facilitate the visual tracking of the blinking object in the non-solid object state, the object 4-2 maybe outlined with dashed lines 4-21. That is, in the example, the dashed line representation of the Glucose object also remains visible when the object is in the non-solid object state. The dashed-line outline can therefore be observed while moving through the inside of the artery.

Further, the shape of the object may still be indicated by using a semitransparent color for the fill-area of the object in the non-solid object state as shown in FIG. 4B. In the example, the sugar cube shape is still visible as a semi-transparent dark grey color. Using the dashed-line outline and/or the semi-transparent color mode in the second Glucose animation rule for rendering the graphic Glucose object in the non-solid object state of the blinking mode significantly improves the traceability of the graphic object while moving through the artery.

FIG. 4C illustrates a third animation rule example of the Glucose animation rule subset for rendering a cluster 4-3 of a plurality of non-blinking Glucose objects indicating a too high Glucose concentration.

In general, a too high blood gas parameter value can be determined by comparing the measured state parameter with a respective predefined high-level threshold for the measured parameter. The cluster may be rendered such that all of the plurality of non-blinking objects (e.g., Glucose objects) are rendered inside a virtual sphere within a predefined cluster radius. The predefined cluster radius can be different for different object types.

In general, a cluster of graphical objects indication a too high value of the respective blood gas state parameter comprises at least two graphical objects. In advantageous embodiments, the number of graphical objects grouped into such a cluster may be at least five.

FIGS. 5A to 5D—Animation Rule Subset for the Electrolyte State Parameters Chloride, Potassium, Calcium, and Sodium FIG. 5A illustrates a first animation rule example of the electrolyte animation rule subset for rendering a two-by-two arrangement (inside the dash-dotted bounding box 5-1) of four electrolyte objects 5-11 to 5-14 with a single non-blinking electrolyte object (a labeled sphere in the example embodiment) for each electrolyte K+, Ca2+, Na+ and Cl—, respectively, indicating normal concentration of the electrolyte parameters. Other representations may be chosen for the electrolyte objects by a person skilled in the art, such as for example, polygonal shaped objects instead of spheres. The two-by-two arrangement is moving through the inside of the artery at substantially the same speed as the Glucose objects. While moving through the artery, the two-by-two arrangement may be rotating in any direction around its center point, and the electrolyte objects may rotate around their center points.

FIG. 5B illustrates a second animation rule example of the electrolyte animation rule subset for rendering the two-by-two arrangement wherein a blinking electrolyte object 5-21 indicates a too low concentration of the respective electrolyte parameter K+. As for all blinking objects, it may be outlined with a blinking line and/or a semi-transparent fill color in the non-solid object state.

FIGS. 5C and 5D illustrate a third animation rule example of the electrolyte animation rule subset for rendering the two-by-two arrangement wherein a replication of a particular non-blinking electrolyte object around the two-by-two arrangement indicates a too high concentration of the respective electrolyte parameter. In FIG. 5C, replications 5-33r of the Na+ object indicate a too high Na+ concentration. The replications may be generated within a predefined radius of a sphere with the center point of the two-by-two arrangement as its center. Alternatively, the replications may be generated within another geometric body (e.g., a cube or cuboid with its center at the center of the two-by-two arrangement). At least one replication is required for indicating a too high electrolyte concentration. Advantageously, at least 5 replications are generated. FIG. 5D illustrates replications 5-44r of the Cl— electrolyte too indicate a to high Cl— concentration.

FIGS. 6A to 6C—Animation Rule Subset for the Hemoglobin State Parameter

FIG. 6A illustrates a first animation rule example of the Hemoglobin animation rule subset for rendering a non-blinking single red blood cell object 6-1, indicating a normal Hemoglobin value. In the example, the red blood cell object has a 3D shape which resembles the real shape of red blood cells. However, other objects (e.g., a disk-like shape) may be used by a skilled person.

FIG. 6B illustrates a second animation rule example of the Hemoglobin animation rule subset for rendering a blinking single red blood cell object 6-2, indicating a too low Hemoglobin value as an indicator for anemia.

FIG. 6C illustrates a third animation rule example of the Hemoglobin animation rule subset for rendering a cluster 6-3 of a plurality of non-blinking red blood cell objects, indicating a too high Hemoglobin value. The red blood cell cluster includes at least two red blood cell objects, and, advantageously, comprises at least 5 red blood cell objects. Again, the cluster may be rendered such that all comprised red blood cell objects are placed with a virtual cluster sphere or other geometric body (e.g., a cube or cuboid). The blood cell cluster moves through the artery at substantially the same speed as the single blood cell objects of FIGS. 6A and 6B.

Figure 7A:
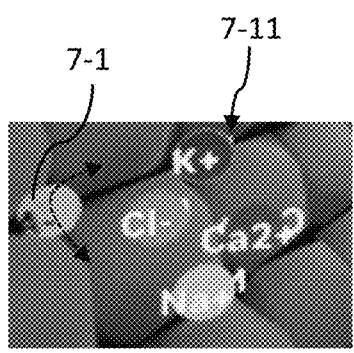
FIGS. 7A to 7C illustrate example rendering results of unspecific anion objects for an anion gap state parameter in accordance with three respective predefined animation rules according to an embodiment.
Figure 7B:
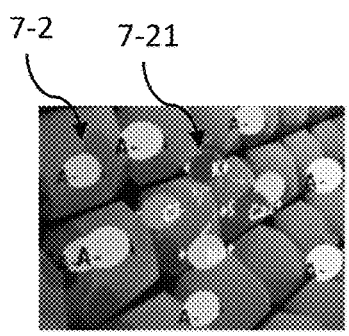
Figure 7C:
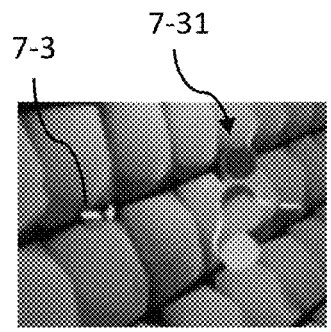

FIGS. 7A to 7C—Animation Rule Subset for an Anion Gap State Parameter

The anion gap animation rule subset renders representations of unspecific anion objects for an anion gap state parameter in accordance with three respective predefined animation rules. The anion gap state parameter is also received from the data source 200 as time series of sampled anion gap state parameter values associated with unspecific anions. The anion gap is not a directly measured blood gas state parameter but a value computed by the data source from other directly measured blood gas state parameters. A person skilled in the art of blood gas analysis knows how to derive the anion gap from measured blood gas state parameters. The mapper 130 maps the anion gap state parameter to a predefined corresponding graphical anion gap representation being distinct from all graphical representations of the remaining state parameters. Finally, the renderer 140 renders the anion gap representation in relation to the two-by-two arrangement for the electrolyte state parameters in accordance with the following anion gap animation rules.

FIG. 7A illustrates a first animation rule example of an anion gap animation rule subset for rendering the two-by-two arrangement 7-11 for the electrolyte state parameters K+, Ca2+, Na+ and Cl— being orbited by an unspecific anion object 7-1 (A-), indicating a normal anion gap. The center of the orbit is located at the center of the two-by-two arrangement 7-11. The orbiting direction (illustrated by dotted double arrow) can be clockwise or anticlockwise. The radius of the orbit of the unspecified anion 7-1 is greater than a predefined electrolyte radius of a bounding sphere (or respective dimensions of other virtual graphic body shapes) used for rendering replications of a particular non-blinking electrolyte object around the two-by-two arrangement 7-11.

FIG. 7B illustrates a second animation rule example of the anion gap animation rule subset for rendering the two-by-two arrangement 7-21 for the electrolyte state parameters being orbited with said radius of the orbit by a plurality 7-2 of unspecific anion objects, indicating a too high anion gap. The plurality of unspecified objects includes at least 5 anion objects and, advantageously, comprises at least five anion objects. In the example of FIG. 7B, nine anion objects are used for the plurality 7-2.

FIG. 7C illustrates a third animation rule example of the anion gap animation rule subset for rendering the two-by-two arrangement 7-31 for the electrolyte state parameters being orbited by a single blinking unspecific anion object 7-3, indicating a too low anion gap.

Figure 8A:
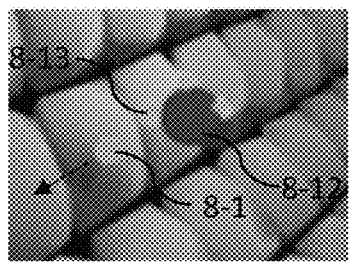
FIGS. 8A to 8C illustrate example rendering results of bound oxygen objects for an oxygen affinity state parameter in accordance with three respective predefined animation rules according to an embodiment.
Figure 8B:
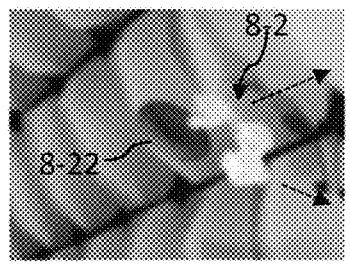
Figure 8C:
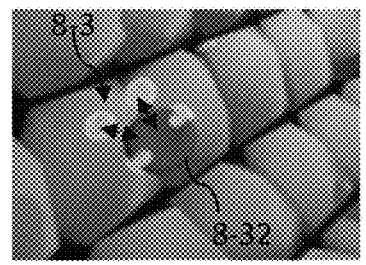

FIGS. 8A to 8C—Animation Rule Subset for an Oxygen Affinity State Parameter

The oxygen affinity animation rule subset renders representations of oxygen objects associated with red blood cell objects for the oxygen affinity state parameter of the patient in accordance with three respective predefined animation rules. The oxygen affinity state parameter is also received from the data source 200 as time series of sampled oxygen affinity state parameter values. The mapper 130 maps the oxygen affinity state parameter to a predefined corresponding graphical oxygen affinity representation being distinct from all graphical representations of the remaining state parameters. Finally, the renderer 140 renders the oxygen affinity representation in relation to a corresponding red blood cell object in accordance with the following oxygen affinity animation rules.

FIG. 8A illustrates a first animation rule example of an oxygen affinity animation rule subset for rendering one oxygen object 8-1 being released by a red blood cell object 8-12 in the course of moving through the artery, indicating normal oxygen affinity. Shortly before the release of oxygen object 8-1, the red blood cell object 8-12 in the example had four bound oxygen objects 8-13 (including object 8-1). However, a blood cell object representing normal oxygen affinity may also have a plurality of bound oxygen objects with less than four bound oxygen objects. FIG. 8A illustrates the rendering result shortly after object 8-1 has been released. The dotted arrow indicates the direction in which the released oxygen object moves away from the blood cell object 8-1. In case the moving direction of the blood cell object through the artery is the same as the moving direction of the released oxygen object 8-1, the rendered speed of the released oxygen object 8-1 is higher than the rendered speed of the associated blood cell object 8-12. In case the moving directions are opposite, the rendered speed of the released oxygen object 8-1 is lower than the rendered speed of the associated blood cell object 8-12. In both case, an effect is rendered which creates the impression that the released oxygen object moves away from its associated blood cell object.

FIG. 8B illustrates a second animation rule example of the oxygen affinity animation rule subset for rendering all oxygen objects 8-2 originally bound to the red blood cell object 8-22 being released by the red blood cell object in the course of moving through the artery, indicating too low oxygen affinity. The dotted arrows indicate that each released oxygen object may move away from the associated blood cell object 8-22 under different angles with regard to the moving direction of the red blood cell object.

FIG. 8C illustrates a third animation rule example of the oxygen affinity animation rule subset for rendering all oxygen objects 8-3 originally bound to the red blood cell object 8-32 with a rubber band animation oscillating between their neutral positions (while being bound to the blood cell object) and a position at a predefined oscillation distance from the red blood cell surface, in the course of moving through the artery, indicating too high oxygen affinity. In the figure, the dotted double arrows indicate the rubber band animation for two of the oxygen objects 8-3. However, the third animation rule is applied to all oxygen object 8-3 associated with the red blood cell object 8-3.

Figure 9A:
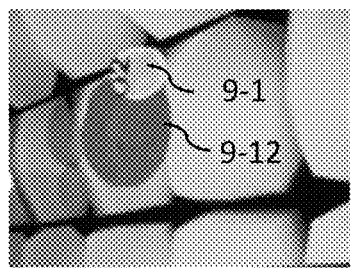
FIG. 9A illustrates an example rendering result of a single red blood cell object with one bound oxygen object for an oxygen saturation state parameter in accordance with a respective predefined animation rule according to an embodiment.
Figure 9B:
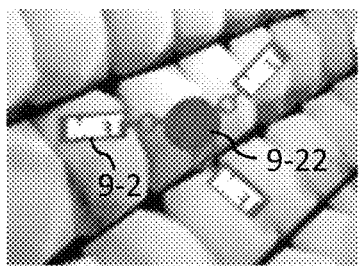
FIG. 9B illustrates an example rendering result of a single red blood cell object with Methemoglobin level labels for an Methemoglobin state parameter in accordance with a respective predefined animation rule according to an embodiment.
Figure 9C:
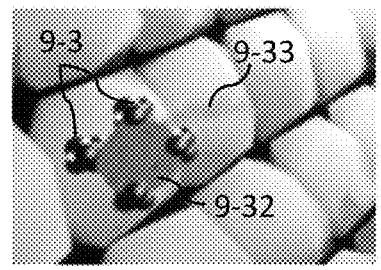
FIG. 9C illustrates an example rendering result of a red blood cell object with a plurality of bound carbonmonoxy objects for an Carbonmonoxy state parameter in accordance with a respective predefined animation rule according to an embodiment.

FIGS. 9A to 9C—Animation Rule Examples for an Oxygen Saturation, Methemoglobin and Carbonmonoxy State Parameters For the oxygen saturation, Methemoglobin and Carbonmonoxy state parameters of the patient, only one animation rule is illustrated for each of these state parameters. However, following description describes an example for the entire respective animation rule set.

The oxygen saturation animation rule subset renders sampled measurement values for an oxygen saturation state parameter of the patient obtained as further time series from the data source. The oxygen saturation state parameter is mapped to a predefined corresponding graphical oxygen saturation representation being distinct from all graphical representations of the remaining state parameters. The rendering is performed in accordance with the following two predefined oxygen saturation animation rules.

FIG. 9A illustrates a first animation rule example of the oxygen saturation animation rule subset for rendering a non-blinking single red blood cell object 9-12 having an alert color with a single bound oxygen object 9-1, indicating a too low oxygen saturation. The alert color is a color clearly distinguishable by the human visual system from the normal red blood cell color. For example, the normal red blood cell color (i.e., the color which is used in all cases where no alert color is used) may be a dark red whereas the alert color may be a bright purple.

The second animation rule example of the oxygen saturation animation rule subset renders a non-blinking single red blood cell object loaded with a plurality of bound oxygen objects as shown in FIG. 6A, indicating a normal oxygen saturation.

The Methemoglobin animation rule subset renders sampled measurement values for a Methemoglobin state parameter of the patient obtained as further time series from the data source. The Methemoglobin state parameter is mapped to a predefined corresponding graphical oxygen saturation representation being distinct from all graphical representations of the remaining state parameters. The rendering is performed in accordance with the following two predefined Methemoglobin animation rules.

FIG. 9B illustrates a first animation rule example of the Methemoglobin animation rule subset for rendering a non-blinking single red blood cell object 9-22 having an alert color with a single bound oxygen object and, in addition, a plurality of Methemoglobin level labels 9-2 (instead of bound oxygen objects), indicating a too high Methemoglobin level with limited oxygen transport capacity. Advantageously, the alert color is the same color as in FIG. 9A.

The second animation rule example of the Methemoglobin animation rule subset renders a non-blinking single red blood cell object loaded with a plurality of bound oxygen objects as shown in FIG. 6A, indicating a normal Methemoglobin level.

The Carbonmonoxy animation rule subset renders sampled measurement values for a Carbonmonoxy state parameter state parameter of the patient obtained as further time series from the data source. The Carbonmonoxy state parameter state parameter is mapped to a predefined corresponding graphical Carbonmonoxy state parameter representation being distinct from all graphical representations of the remaining state parameters. The rendering is performed in accordance with the following two predefined Carbonmonoxy state parameter animation rules.

A first animation rule example of the Carbonmonoxy state parameter animation rule subset renders a non-blinking single red blood cell object loaded with a plurality of bound oxygen objects as shown in FIG. 6A, indicating a normal Carbonmonoxy state parameter level.

FIG. 9C illustrates a second animation rule example of the Carbonmonoxy state parameter animation rule subset for a single red blood cell object 9-32 having an alert color with a plurality of bound carbonmonoxy objects 9-3 instead of the bound oxygen objects (i.e., replacing the bound oxygen objects of the first Carbonmonoxy animation rule), and with the red blood cell leaving behind a trail 9-33 of fire (or smoke) in the course of moving through the artery. Advantageously, the alert color is the same color as in FIG. 9A. In the example of FIG. 9C, carbonmonoxy objects are rendered by using black spheres having a size comparable to the size of the oxygen objects. Other icons, such as for example a black dumbbell for a carbonmonoxy object may be used.

Figure 10A:
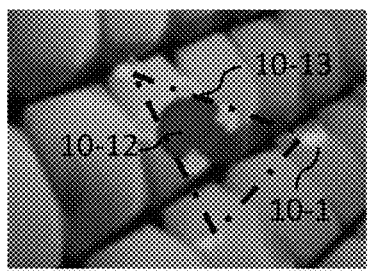
FIGS. 10A, 10B illustrate example rendering results of a single red blood cell object with unbound oxygen objects for an Oxygen Partial Pressure state parameter in accordance with two respective predefined animation rules according to an embodiment.
Figure 10B:
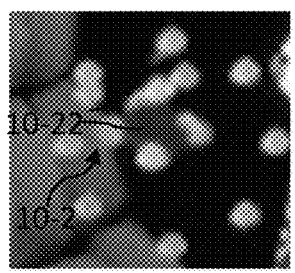

FIGS. 10A, 10B—Animation Rule Subset for an OPP State Parameter

The OPP animation rule subset renders representations of unbound oxygen objects associated with red blood cell objects for the OPP state parameter of the patient in accordance with three respective predefined animation rules. The Oxygen Partial Pressure state parameter is also received from the data source 200 as time series of sampled OPP values. The mapper 130 maps the OPP state parameter to a predefined corresponding graphical OPP representation being distinct from all graphical representations of the remaining state parameters. Finally, the renderer 140 renders the OPP representation in accordance with the following OPP animation rules.

A first animation rule example of the OPP animation rule subset renders a non-blinking single red blood cell object indicating a normal OPP level. For example, a rendering result like in FIG. 6A also indicates a normal OPP level. It is to be noted that for indicating the OPP level, the number of bound oxygen objects of the respective blood cell play no role. That is, even a single non-blinking red blood cell object without any bound oxygen objects indicates a normal OPP level.

FIG. 10A illustrates a second animation rule example of the OPP animation rule subset rendering a non-blinking single red blood cell object 10-12 surrounded by a cluster with at most a predefined low-OPP-level-number of unbound blinking oxygen objects 10-1, indicating a low OPP level. In the example, the low-OPP-level-number is three. An unbound oxygen object 10-1 is located at each edge of the dash-dotted triangle 10-13 representing the cluster. Alternatively, the OPP low-level-number may be set to two or four. The unbound blinking oxygen objects 10-1 are placed within a virtual 3D geometric body centered at the center of the associated blood cell object. The distance of the unbound blinking oxygen objects 10-1 to the blood cell object is greater than the oscillation distance in FIG. 8C.

FIG. 10B illustrates a third animation rule example of the OPP animation rule subset rendering a non-blinking single red blood cell 10-22 object surrounded by a cluster 10-2 with at least a predefined high-OPP-level-number of unbound non-blinking oxygen objects indicating a high OPP level. The difference between high-OPP-level-number and the low-OPP-level number is at least five. The unbound non-blinking oxygen objects of cluster 10-2 are placed within a virtual 3D geometric body centered at the center of the associated blood cell object. The distance of the unbound non-blinking oxygen objects 10-1 to the blood cell object is greater than the oscillation distance in FIG. 8C.

Figure 11A:
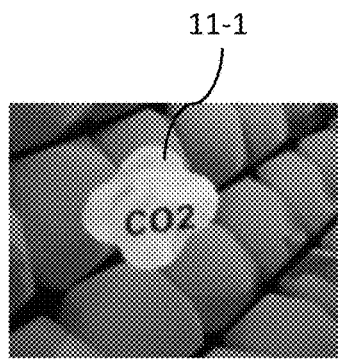
FIGS. 11A to 11C illustrate example rendering results of CO2 objects for a CO2 partial pressure state parameter in accordance with three respective predefined animation rules according to an embodiment.
Figure 11B:
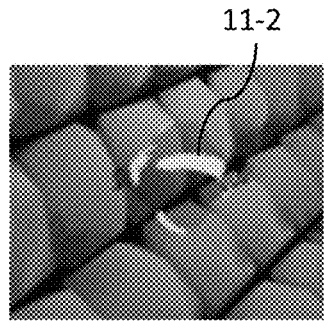
Figure 11C:
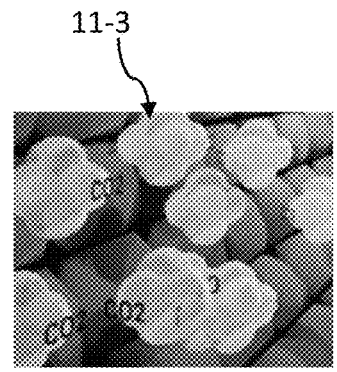

FIGS. 11A to 11C—Animation Rule Subset for a CO2 Partial Pressure State Parameter The CO2 partial pressure animation rule subset renders representations of the patient's CO2 partial pressure in accordance with three respective predefined animation rules. The CO2 partial pressure state parameter is also received from the data source 200 as time series of sampled CO2 partial pressure values. The mapper 130 maps the CO2 partial pressure state parameter to a predefined corresponding graphical CO2 partial pressure representation being distinct from all graphical representations of the remaining state parameters. Finally, the renderer 140 renders the CO2 partial pressure representation in accordance with the following CO2 partial pressure animation rules.

FIG. 11A illustrates a first animation rule example of the CO2 partial pressure animation rule subset for rendering a non-blinking single CO2 object indicating a normal CO2 partial pressure. In the example, CO2 object 11-1 is shaped like cloud and carries a label 'CO2' which facilitates the association with the CO2 state parameter. Other graphic objects, such as for example a symbol reflecting the chemical structure of CO2, may be selected as representation of the CO2 state parameter. The CO2 objects move through the inside of the artery at a speed comparable to the speed of the red blood cell objects.

FIG. 11B illustrates a second animation rule example of the CO2 animation rule subset for rendering a blinking single CO2 object indicating a too low CO2 partial pressure.

FIG. 11C illustrates a third animation rule example of the CO2 animation rule subset for rendering a cluster 11-3 of a plurality of non-blinking CO2 objects indicating a too high CO2 partial pressure. Again, the CO2 objects of the cluster 11-3 are all rendered within a 3D virtual geometric body with predefined CO2 object specific dimensions. The cluster 11-3 moves at approximately the same speed as the CO2 objects of FIG. 11A and FIG. 11B. The cluster includes at least two CO2 objects. Advantageously, the cluster comprises at least 5 CO2 objects.

FIGS. 12A to 12D—Animation Rule Examples for a Plasma Osmolarity State Parameter In a further optional embodiment, the Plasma Osmolarity (PO) state parameter is taken into account. The PO state parameter is rendered in a different manner than the previously described blood gas state parameters in that the rendered objects do not move through the artery from the back of the tunnel to its front (or vice versa) with a given rendered flow speed causing the impression of the patient's blood flow. Rather, graphical PO representations are rendered such that the impression is created that the objects are diffusing through the vessel wall of the artery. For this rendering task, the system receives via its interface from the data source further time series of sampled measurement values for the PO parameter of the patient. The mapper module maps the PO state parameter to a predefined corresponding graphical PO representation being distinct from all graphical representations of the remaining state parameters. The renderer renders, in the virtual 3D tunnel shaped scene representing the inside of the artery, animated visualizations of graphical PO representations in accordance with predefined PO animation rules of a PO animation rule subset.

Figure 12A:
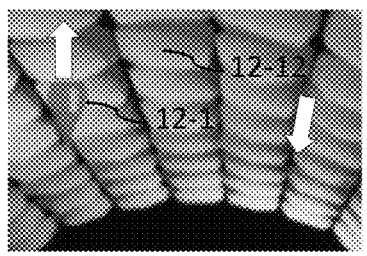
FIGS. 12A to 12E illustrate example rendering results of droplet objects for a Plasma Osmolarity state parameter in accordance with three respective predefined animation rules according to an embodiment.

FIG. 12A illustrates a first animation rule example of the PO animation rule subset for rendering a plurality of droplet objects 12-1 diffusing in and out (white arrows) through the blood vessel wall 12-12 of the artery, indicating normal Plasma Osmolarity, wherein each droplet object has a shape indicating the diffusion direction of the respective droplet object. In the example, only droplet object 12-1 is clearly visible as an out-diffusing object because of the black and white visualization. However, in a color visualization, at the start location of the arrow illustrating the diffusion direction into the vessel, an second droplet object is being formed with an in-diffusing direction. Normal PO values may be represented by an animation where only a low number of droplets is diffusing in and out in alternating manner.

Figure 12B:
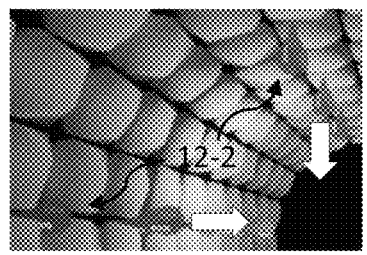
Figure 12C:
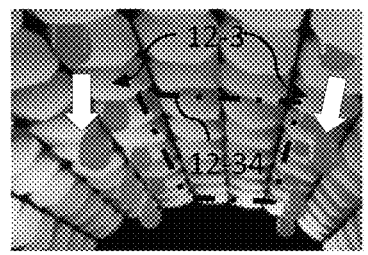

FIGS. 12B, 12C illustrate a second animation rule example of the PO animation rule subset for rendering a plurality of droplet objects 12-2, 12-3 only diffusing into the artery through the blood vessel wall, indicating a too low Plasma Osmolarity. The two figures illustrate an implementation where rows of droplets continuously diffuse into the inner of the artery. One row of droplet objects may also be used with at least two droplets in the row. Advantageously, the number of droplet rows is selected such that at least one vessel row is rendered in each of the top, right, left and bottom vessel wall sections. Advantageously, a droplet row comprises at least five in-diffusing droplets. Alternative implementations are seen as equivalents to the example implementation in FIG. 12*. For example, instead of droplet rows, droplet areas, such as rectangles (cf. dash-dotted frame 12-34 in FIG. 12C), circles, triangles, etc., could be defined for the vessel wall for rendering the plurality of in-diffusing droplets.

Figure 12D:
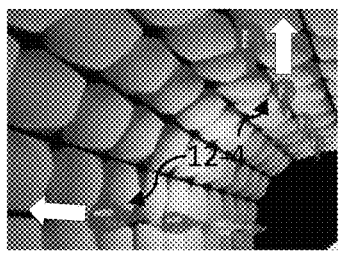
Figure 12E:
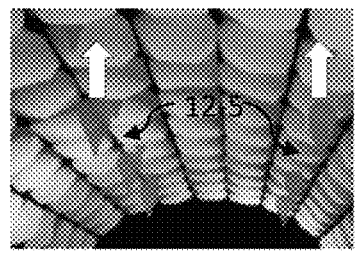

FIGS. 12D, 12E illustrate a third animation rule example of the PO animation rule subset for rendering a plurality of droplet objects 12-4, 12-5 only diffusing out of the artery through the blood vessel wall, indicating a too high Plasma Osmolarity. Similar rendering alternatives may be used for the out-diffusing droplets as described for the in-diffusing droplets.

FIGS. 13A to 13I—Animation Rule Examples for Acid-Base Balance State Parameters of the Patient In a further optional embodiment, Acid-Base Balance state parameters of the patient are taken into account.

In this embodiment, the interface of the system further receives, from the data source, further time series of sampled measurement values for Acid-Base Balance state parameters of the patient. These Acid-Base Balance state parameters may comprise the patient's pH level, bicarbonate concentration, base excess level, and/or lactate concentration. The mapper module maps each Acid-Base Balance state parameter to a predefined corresponding graphical Acid-Base Balance representation being distinct from all graphical representations of the remaining state parameters. The renderer renders, in the virtual 3D tunnel shaped scene representing the inside of the artery, animated visualizations of the graphical Acid-Base Balance representations by using an animated balance object placed at a fixed location at the bottom vessel wall of the artery, in accordance with predefined Acid-Base Balance animation rules. The balance object 13-1 in FIG. 13A has a first weighing pan 13-1*a* associated with acid blood gas parameters (acid weighing pan), and a second weighing pan 13-1*b* associated with base blood gas parameters (base weighing pan). The balance in FIG. 13* is always the same balance object in different animation states dependent of the patient's current Acid-Base Balance state parameters.

Figure 13A:
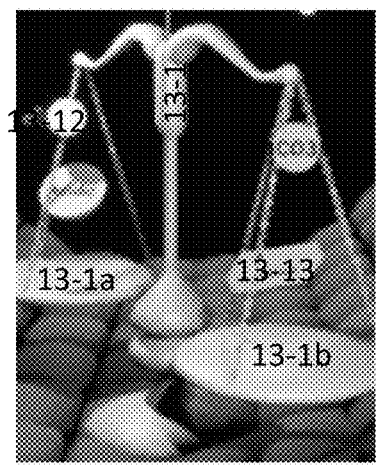
FIGS. 13A to 13I illustrate example rendering results of Acid-Base Balance objects various Acid-Base Balance state parameters in accordance with nine respective predefined animation rules according to an embodiment.
Figure 13B:
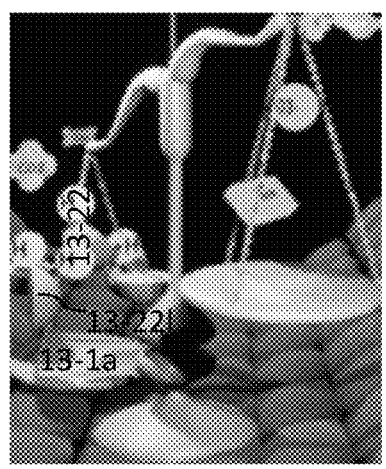
Figure 13C:
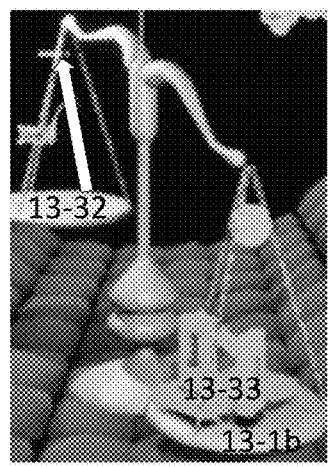

FIGS. 13A to 13C show animation rule examples of the ph animation rule subset for indicating the pH level of the patient.

In FIG. 13A, a first animation rule of the ph animation rule subset renders a non-blinking single H+ object 13-12 associated with the acid weighing pan 13-1$a$ of the balance object 13-1, and a non-blinking unspecific base object 13-13 associated with the base weighing pan 13-1$b$ of the balance object, with both weighing pans being balanced, indicating a normal pH level. It is to be noted that the movement of the weighing pans into low or high positions is exclusively animated by the ph animation rule subset. The other Acid-Base Balance state parameters have no impact on the position of the weighing pans. In the example implementation, an H+ object is rendered as a yellow sphere to represent a single proton. The unspecific base object is rendered with a shape resembling a piece of soap. Of course, a skilled person may choose other graphical representations which are associated by a user with acid and base, respectively.

In FIG. 13B, a second animation rule of the ph animation rule subset renders a cluster 13-22 of a plurality of non-blinking H+ objects associated with the acid weighing pan 13-1$a$ wherein the acid weighing pan is down, indicating a too low pH level. In other words, the too high ph level of the patient is emphasized by the acid weighing pan being down and a cluster of at least two non-blinking H+ objects. In the example, the ph value representation is even more reinforced by associating each H+ object with a graphical representation of a cut lemon half 13-221.

In FIG. 13C, a third animation rule of the ph animation rule subset renders a blinking H$^+$ object 13-32 associated with the acid weighing pan wherein the base weighing pan is down, indicating a too high pH level with alkaline components predominating. The cluster 13-33 of a plurality of non-blinking unspecific base objects associated with the base weighing pan 13-1$b$ has no impact on the balance state of the balance. With the base weighing pan being down, a too high ph level is indicated independent of any graphical object associated with the acid weighing pan. The same way the acid weighing pan being down indicates a too low ph level independent of any graphical object associated with the base weighing pan.

Figure 13D:
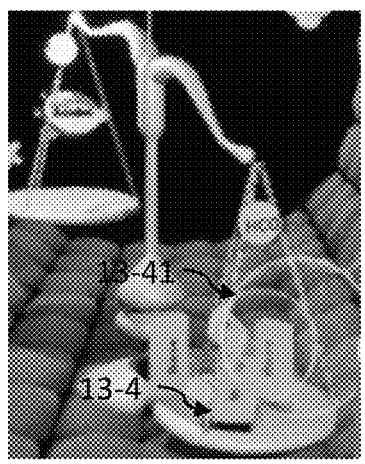
Figure 13E:
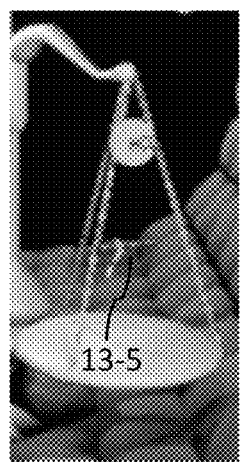

FIGS. 13D and 13E show animation rule examples of the base excess level animation rule subset for indicating a base excess level state parameter of the patient.

FIG. 13D illustrates a first animation rule example of the base excess level animation rule subset for rendering a cluster 13-4 of a plurality of non-blinking unspecific base objects associated with the base weighing pan, the cluster 13-4 continuously releasing soap bubbles 13-41, indicating too high base excess.

FIG. 13E illustrates a second animation rule example of the base excess level animation rule subset for rendering a blinking single unspecific base object 13-5 associated with the base weighing pan, indicating too low base excess.

Figure 13F:
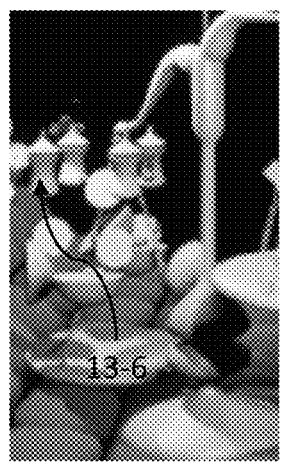

FIG. 13F illustrates a first animation rule example of a lactate animation rule subset for rendering the lactate concentration state parameter of the patient, wherein a cluster 13-6 of a plurality of non-blinking milk bottle objects associated with the acid weighing pan indicates a too high value of lactate concentration. In the example, the lactate state parameter is represented by milk bottle representations as used for feeding babies. Other graphic representations being associated with lactate (e.g., standard milk bottles, milk packs, little cow icons, etc.) may be used instead.

Any other balance representation indicates a normal lactate concentration of the patient.

Figure 13G:
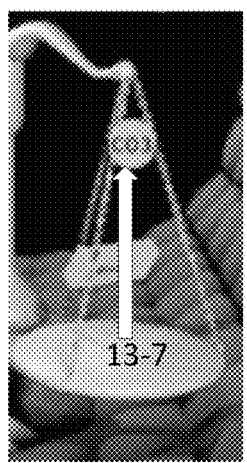
Figure 13H:
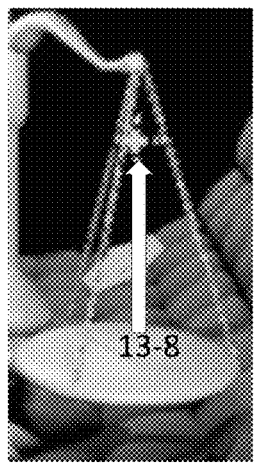
Figure 13I:
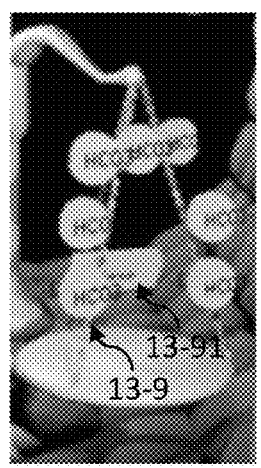

FIGS. 13G to 13I show animation rule examples of the bicarbonate animation rule subset for indicating the bicarbonate concentration state parameter of the patient.

In FIG. 13G, a first animation rule of the bicarbonate animation rule subset renders a non-blinking single HCO3- object 13-7 associated with the base weighing pan, indicating normal bicarbonate concentration of the patient. In the example, the HCO3- object 13-7 has a respective label and is rendered as a sphere of similar size as the H+ sphere object. However, the rendering color for objects associated with the base weighing pan is in a base color range (e.g., light blue colors) whereas the rendering color for objects associated with the acid weighing pan is in an acid color range (e.g., light grey to yellow colors). In the example implementation of FIG. 13*, the HCO3- bicarbonate objects are rendered above the unspecific base objects but such that the bicarbonate objects are still clearly associated with the base weighing pan.

In FIG. 13H, a second animation rule of the bicarbonate animation rule subset renders a blinking single HCO3- object 13-8 associated with the base weighing pan, indicating too low bicarbonate concentration of the patient.

In FIG. 13I, a third animation rule of the bicarbonate animation rule subset renders a cluster 13-9 of a plurality of non-blinking HCO3- objects associated with the base weighing pan, indicating a too high bicarbonate concentration. The cluster 13-9 is rendered such that all HCO3- objects of the cluster are clearly associated with the base weighing pan. For example, all cluster objects may be placed between the base weighing pan and its corresponding balance beam. The cluster comprises at least two HCO3- objects and may also enclose one or more unspecific base objects 13-91.

Study Results

Acid-base homeostasis is critical for all physiological processes in the body and is routinely evaluated using arterial blood gas (ABG) analysis. The conventional presentation of ABG results requires the interpretation of many text elements and numbers, which does not lend itself to intuitive comprehension. To optimize the presentation of the results for the specific strengths of human perception, the herein disclosed animated graphical representation (AGR) of ABG results was tested in a study which compared the human perception based on the animated model with the perception based on a conventional result printout. Seventy physicians from three European university hospitals participated in a computer-based simulation study. Initially, after an educational video, the participants' ability to assign individual AGR visualizations to their corresponding ABG parameters was tested. As the primary outcome, a test was performed on the caregivers' ability to correctly diagnose simulated clinical ABG scenarios with AGR or conventional ABG printout. For user feedback, participants rated their agreement to statements at the end of the study. Physicians correctly assigned 90% of the individual AGR visualizations. Regarding the primary outcome, the participants made the correct diagnosis 86% of the time using AGR compared to 68% when using the conventional ABG printout. A mixed logistic regression model showed an odds ratio for correct diagnosis of 3.4 (95% CI 2.00-5.79, $p<0.001$) and an odds ratio for perceived diagnostic confidence of 1.88 (95% CI 1.67-2.11, $p<0.001$) in favor of AGR. A linear mixed model showed a coefficient for perceived workload of −3.2 (95% CI −3.77 to −2.64) in favor of AGR. Fifty-one of 70 (73%)

participants agreed or strongly agreed that AGR was easy to use and 55/70 (79%) agreed that it was fun to use. In conclusion, AGR improved physicians' ability to diagnose ABG results. It also increased perceived diagnostic confidence and reduced perceived workload. Participants rated their experience positively.

Introduction

Arterial blood gas analysis is the diagnostic standard to detect imbalances in patients' acid-base equilibrium, gas exchange, and electrolyte status. The ability of modern ABG devices to measure a large variety of parameters from samples containing only a few milliliters of blood automatically, quickly, accurately and repeatedly represents a tremendous technological achievement.

However, to take full advantage of the specific strengths of the human perceptual system, prior art ABG devices still have room for optimization with respect to how they present diagnostic information. Prior art ABG result printouts include approximately 20 rows of tabular data, each including a parameter name, value, measurement unit, and expected normal range. Extracting information from such a printout requires caregivers to read and mentally translate a substantial quantity of textual and numerical data elements and integrate the derived meaning into their pre-existing mental models of ABG analysis. In these mental constructs, they assign the various parameters to specific physiological functions or abnormalities. These mental models vary widely among caregivers, which is reflected in the different orders in which caregivers read the parameters and in the different meanings they ascribe to them in different situations.

Moreover, this cognitively demanding process of interpretation happens in clinical environments where caregivers must deal with various factors that negatively affect their performance, such as information overload, distractions, and fatigue, which makes fostering situational awareness particularly challenging. Situational awareness is a three-step concept consisting of perceiving the relevant data elements in a situation, understanding their meaning, and projecting the situation's significance into the near future. High situational awareness allows to make decisions that are optimally adapted to a given situation and to perform appropriate actions. Research has identified situational awareness breakdowns as the primary cause of adverse events in anesthesia critical incident reporting system cases and malpractice claims and found strong evidence for a link between improving situational awareness and improving performance. For example, cognitive aids like the World Health Organization safety checklists improve situation awareness and outcomes, and situation awareness-oriented design improves diagnostic performance.

The animated visualization of the ABG results using the herein disclosed AGR approach optimizes the information presented in the ABG results for achieving situational awareness.

In this study, the results of a multimodal quantitative and survey study of AGR are reported. A test of was performed on the primary hypothesis that participants make a higher number of correct diagnoses in simulated clinical scenarios with AGR than with conventional ABG result printouts. Further, the technology's effects on participants perceived diagnostic confidence and workload was examined. Furthermore, the learnability of AGR and conducted a survey to gain insights into caregivers' acceptance of the concept was evaluated.

Methods

AGR was developed using the gaming engine Unreal Engine 4 (Epic Games, Inc., Raleigh, North Carolina, USA). The version evaluated in this study is a software prototype simulating ABG results for the users.

AGR is a computer animation showing a virtual model of any given ABG situation by visualizing the ABG parameters and their interactions as intuitive 3D icons. AGR was developed based on the principles of user-centered and situational awareness-oriented design. It follows the goal of situational awareness-oriented interface design: to convey the information needed by the caregivers as quickly as possible and with the lowest cognitive effort.

To be recognizable as a model of the ABG result and thus support global situational awareness, AGR positions the caregivers' viewpoint inside an arterial blood vessel as described in detailed in the preceding description. The individual parameter visualizations flow through this vessel. Like the artery, these visualizations have a logical commonality with the reality they intend to model. For example, in AGR, high plasma osmolarity is indicated by a high number of $H2O$ molecules flowing into the blood vessel through its wall. AGR groups parameter visualizations according to their function or place of action in actual blood. For example, oxygen and carbon monoxide molecules bind to the erythrocytes' oxygen-binding sites, as they would in reality. This aims to facilitate the simultaneous perception and understanding of the status of interconnected parameters. To make critical signals visually salient, a logic was selected for these animations that also has a meaningful relation to reality. Parameter visualizations that are too low become semi-transparent (or greyed-out), dashed and blinking, which are visual clues used to indicate a missing or non-available part. Parameter visualizations that are too high appear in higher numbers than when normal. The reduction of information complexity by classifying parameters as either too low, normal or too high is a further situational awareness-oriented design principle being used. In the conventional ABG result printouts, the care providers perform this classification themselves with the help of the normal reference values provided.

Study Design and Participants

This was an investigator-initiated, multicenter, randomized, prospective, computer-based, within-subject simulation study comparing AGR and conventional ABG result printouts. Anesthesiologists and intensivists in training (resident physicians) or already board-certified (staff physicians) were included. We recruited participants from three hospitals, the University Hospitals Zurich in Switzerland, and Frankfurt and Wuerzburg in Germany.

The study consisted of two parts. In the first part, it was investigated how well the participants assigned individual VB visualizations to their corresponding ABG analysis parameters after a short educational video. In the second part of the study, AGR results were compared with conventional ABG result printouts testing the hypothesis that using AGR enables participants to improve their perception of individual parameters, make a higher number of correct diagnoses, perceive higher diagnostic confidence and lower workloads.

Study Procedure and Outcome Measures

Firstly, the participants were presented an educational video. After watching the video, the participants had time to ask questions or rewatch video sections.

For part one of the study, investigating the assignment of AGR visualizations to their corresponding or intended ABG parameters (visualization assignment), the participants were shown 15-second-long AGR sequences, in each of which precisely one ABG parameter was outside the norm. It was then asked which parameter it was and in which direction ("too high" or "too low"). If a parameter and the direction of its deviation were correctly assigned, a correct assignment was counted for the visualization in question. For 14 of the total 18 parameters, an AGR sequence was displayed with values that were too low and too high. Parameters that deviated in a single direction of clinical relevance were displayed only in this direction (i.e., lactate, methemoglobin, carboxyhemoglobin, and oxygen saturation). Thus, there were 32 sequences per participant, which were presented in randomized order (ReseachRandomizer version 4.0; http://www.randomizer.org).

Part two of the study compared ABG results shown as AGR representations to the same ABG results shown as conventional ABG result printouts, evaluating the primary outcome, correct clinical diagnosis, as binary variable.

The participants were shown scenarios with multiple deviations, each matching a clinical diagnosis. The scenarios always lasted 15 seconds, after which the screen turned black. 2×3 scenarios were shown to each participant, once with AGR and once as a conventional ABG result printout enabling three within-subject comparisons per participant. After each scenario, the participants were requested to assign the displayed ABG results to one of 12 clinical diagnoses and to rate for all ABG parameters whether they were too low, within normal range or too high. In addition, participants rated after each scenario, their diagnostic confidence and perceived workload. The three presented scenarios originated from a pool of six different scenarios. Scenario selection, order, and type of presentation (AGR or conventional ABG result printout) were randomized. As a secondary outcome, the difference in clinical diagnosis performance between VB and conventional ABG printout as a function of participants' individual performance with conventional ABG was examined to evaluate whether AGR can particularly support caregivers who perform less well in conventional ABG.

A further secondary outcome was parameter perception, defined as the number of correctly perceived ABG parameters. Participants had to indicate the status of each parameter visualization (18 in each scenario). Further secondary outcomes included diagnostic confidence and perceived workload. The participants rated their subjective diagnostic confidence on a 4-point Likert scale (from very unconfident to very confident) and perceived workload using the National Aeronautics and Space Administration Task Load Index (NASA-TLX; from 0-100) [Hart S G, Staveland L E. Development of NASA-TLX (Task Load Index): Results of Empirical and Theoretical Research. Advances in psychology 1988; 52: 139-83.].

Before leaving, participants rated four general statements on a 5-point Likert scale (from strongly disagree to strongly agree) to capture their impressions about AGR. All responses were entered into a survey (Harvest your data, Wellington, New Zealand) on an iPad (Apple Inc., Cupertino, CA, USA).

Statistical Analysis

For descriptive statistics, we show medians and interquartile ranges for continuous data and numbers and percentages for categorical data.

To analyze the outcome of part one of the study, visualization assignment, mixed logistic regression models were used with a random intercept per participant and the respective parameter as covariate to estimate the proportion of correct visualization assignment (correct assignment of parameters and parameter deviations) considering that there were repeated measurements of the same persons that are not independent. The results are shown as estimated percentages with confidence intervals.

To analyze the outcomes of part two of the study, correct clinical diagnosis, parameter perception and diagnostic confidence, also mixed logistic regression models with a random intercept per participant were used. To further explore the difference in clinical diagnosis performance between AGR and conventional ABG printout the participants' individual differences between the number of correct answers using conventional ABG or AGR in the same scenario were analyzed using a linear mixed model with random intercept per participant. Note that in this case the ordering of the two methods (i.e., whether VP or ABG came first) was ignored, but this should not have much effect because of the randomization. To analyze the overall NASA-TLX, which represents perceived workload as a continuous outcome a linear mixed model was run with random intercept for each participant. All models were adjusted for potentially relevant covariates such as age, gender, work experience, study centre, and scenario.

Sample Size Calculation

The sample size was calculated using data from part one of the study, i.e., the estimated proportion of correctly assigned visualization parameters. It was calculated that in order to construct a 95% confidence interval for an estimated proportion that extends no more than 10% in either direction, 35 participants are needed if the true proportion is 90%, and 62 participants are needed if the true proportion is 80%, so that the final sample size of 70 is enough to obtain the desired precision.

To generate the statistical report, R version 4.0.5 (R Foundation for Statistical Computing, Vienna, Austria) was used. To create figures and graphs, GraphPad Version 9.0.3 (GraphPad Software Inc., California, USA) was used. A value of p-value<0.05 was considered to indicate statistical significance.

Results

Between April and May 2022, a total of 70 participants were recruited drawn from the three study centers' anesthesia staff.

Study Part 1

In part one, visualization assignment was investigated and it was found that across all participants and all tested parameter visualizations and deviations of AGR, 2011/2240 (90%) visualizations were correctly assigned. The mixed logistic regression model yielded an estimated proportion of correct visualization assignments per participant of 91.5% (95% CI 89.5% to 93.2%). To illustrate which parameter visualizations were particularly well or less well assigned, Table 1 shows the number and percentages of correct visualization assignment per parameter and the results of the mixed logistic regression model per parameter.

TABLE 1

Correct visualization assignments per parameter (=parameter and deviation correctly assigned). Column two shows the numbers and percentages of correct visualization assignments. Column three shows the estimated proportions according to the mixed logistic regression model per parameter, which considered repeated non-independent measurements from the same persons.

| Parameter | Number (percent) of correct visualisation assignment | Estimated proportion (95% CI) of correct visualisation assignment |
| --- | --- | --- |
| Lactate | 70 of 70 (100) | 1.00 |
| Methaemoglobin | 70 of 70 (100) | 1.00 |
| Partial pressure of carbon dioxide | 140 of 140 (100) | 1.00 |
| Osmolarity | 127 of 140 (91) | 0.99 (0.96 to 1.00) |
| Glucose | 138 of 140 (99) | 0.99 (0.97 to 1.00) |
| Anion gap | 133 of 140 (95) | 0.98 (0.95 to 0.99) |
| Chloride | 137 of 140 (98) | 0.98 (0.95 to 0.99) |
| Potassium | 137 of 140 (98) | 0.98 (0.95 to 0.99) |
| Calcium | 134 of 140 (96) | 0.97 (0.94 to 0.99) |
| Bicarbonate | 134 of 140 (96) | 0.97 (0.93 to 0.99) |
| Sodium | 133 of 140 (95) | 0.96 (0.92 to 0.98) |
| Carboxyhaemoglobin | 64 of 70 (91) | 0.94 (0.85 to 0.97) |
| pH value | 115 of 140 (82) | 0.94 (0.89 to 0.97) |
| Haemoglobin | 121 of 140 (86) | 0.89 (0.82 to 0.93) |
| Partial pressure of oxygen | 109 of 140 (78) | 0.87 (0.80 to 0.92) |
| P50 | 105 of 140 (75) | 0.86 (0.78 to 0.91) |
| Base excess | 104 of 140 (74) | 0.78 (0.69 to 0.85) |
| Oxygen saturation | 40 of 70 (57) | 0.58 (0.44 to 0.70) |

Study Part 2

Figure 14A:
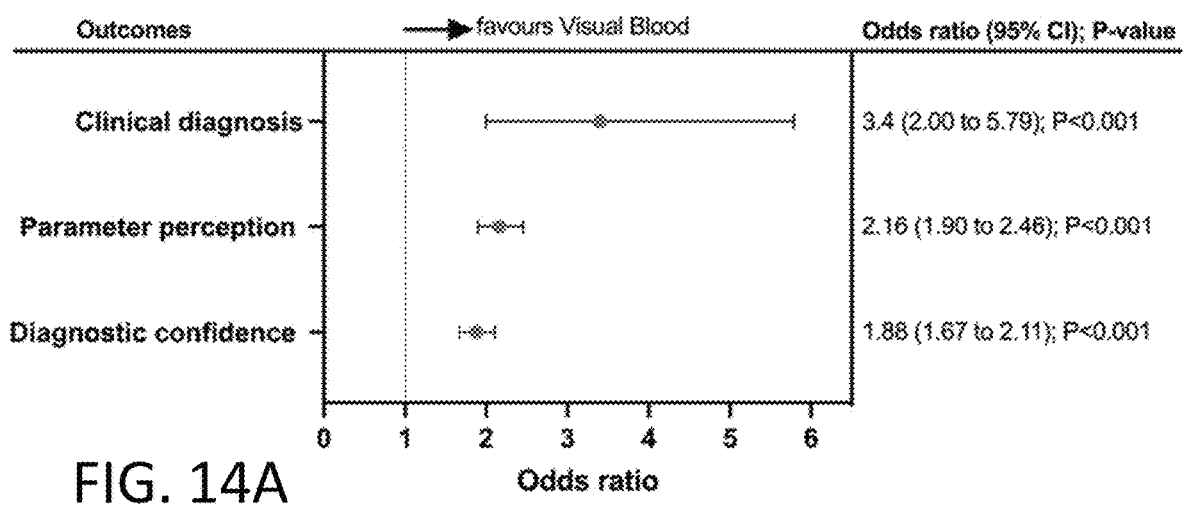
FIGS. 14A, 14B, and FIGS. 15A to 15C show study results obtained from a study performed to validate the herein disclosed blood gas state parameter rendering approach with a group of medically trained users.
Figure 14B:
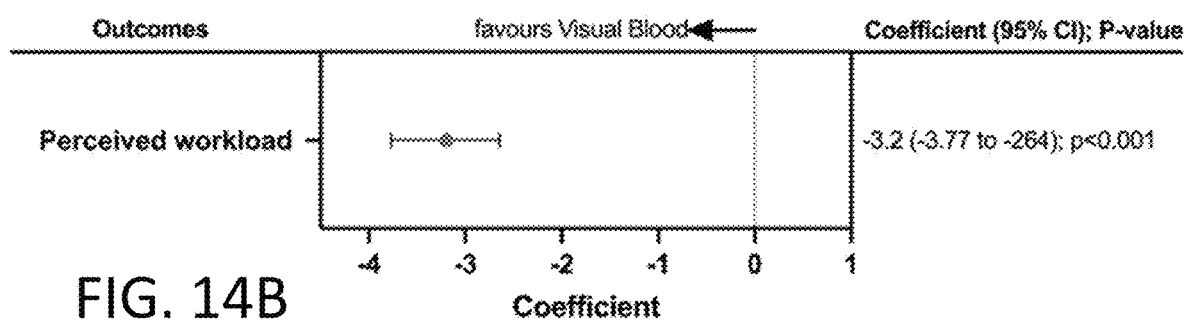
Figure 15A:
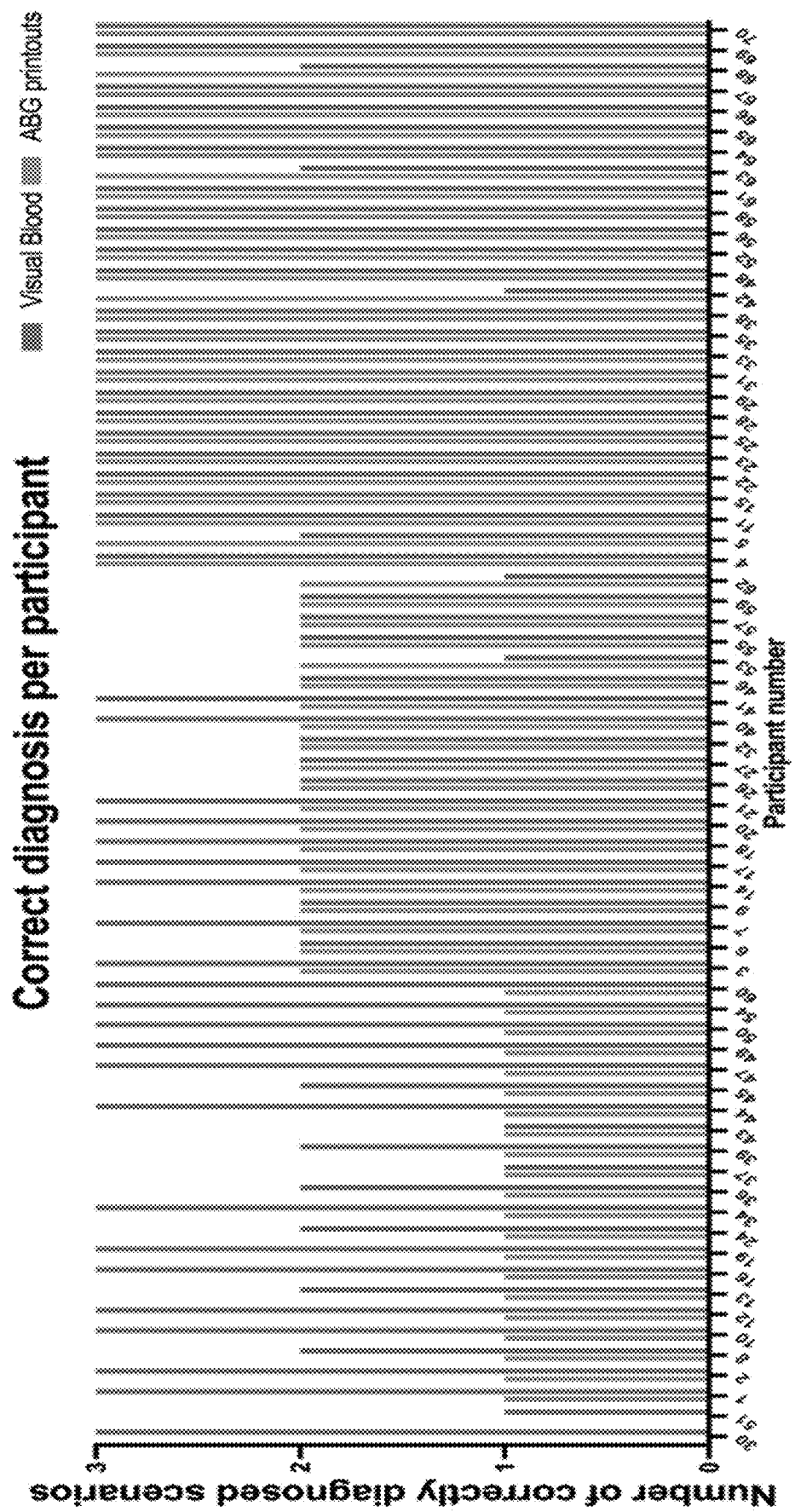
Figure 15B:
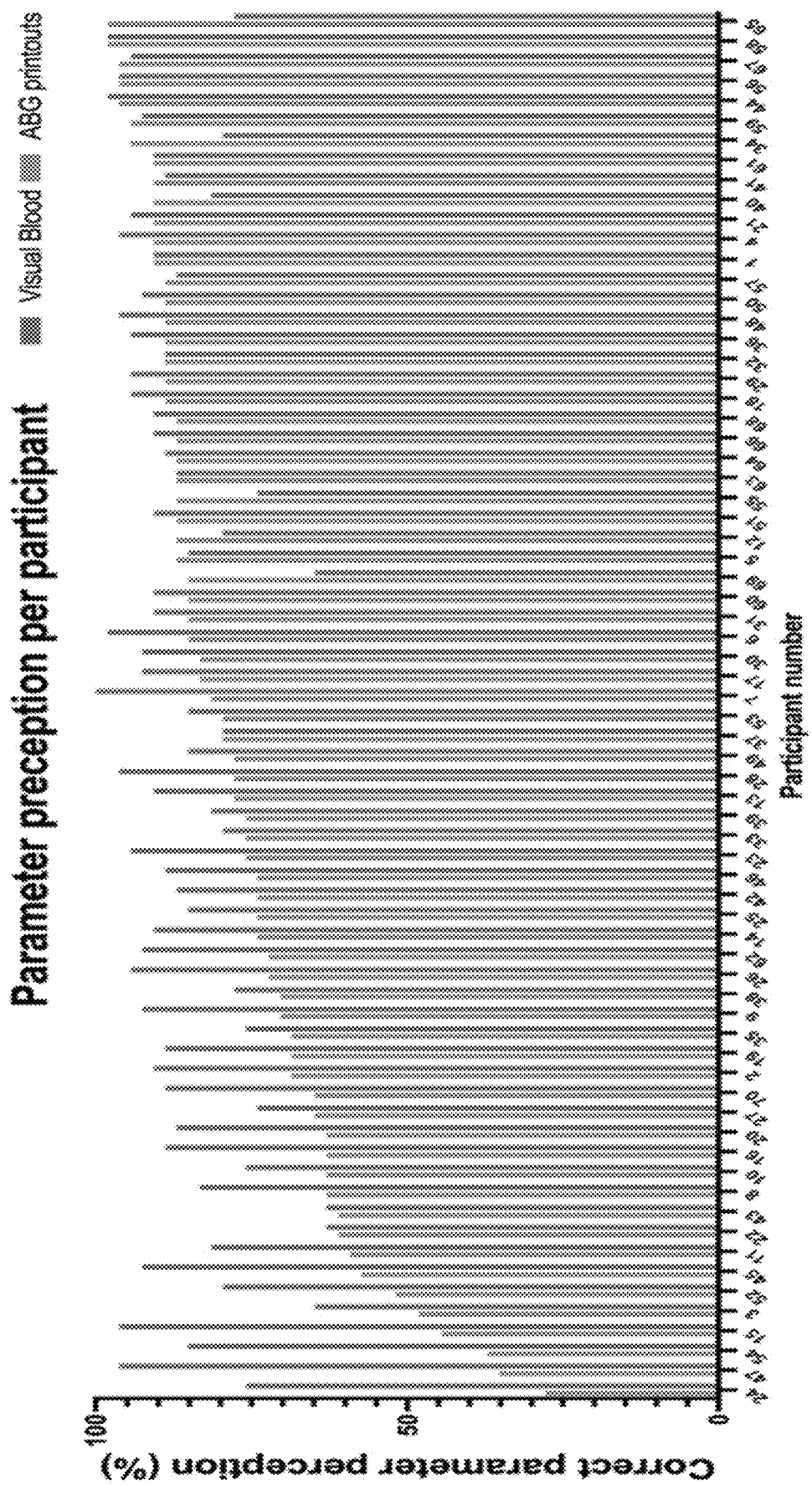
Figure 15C:
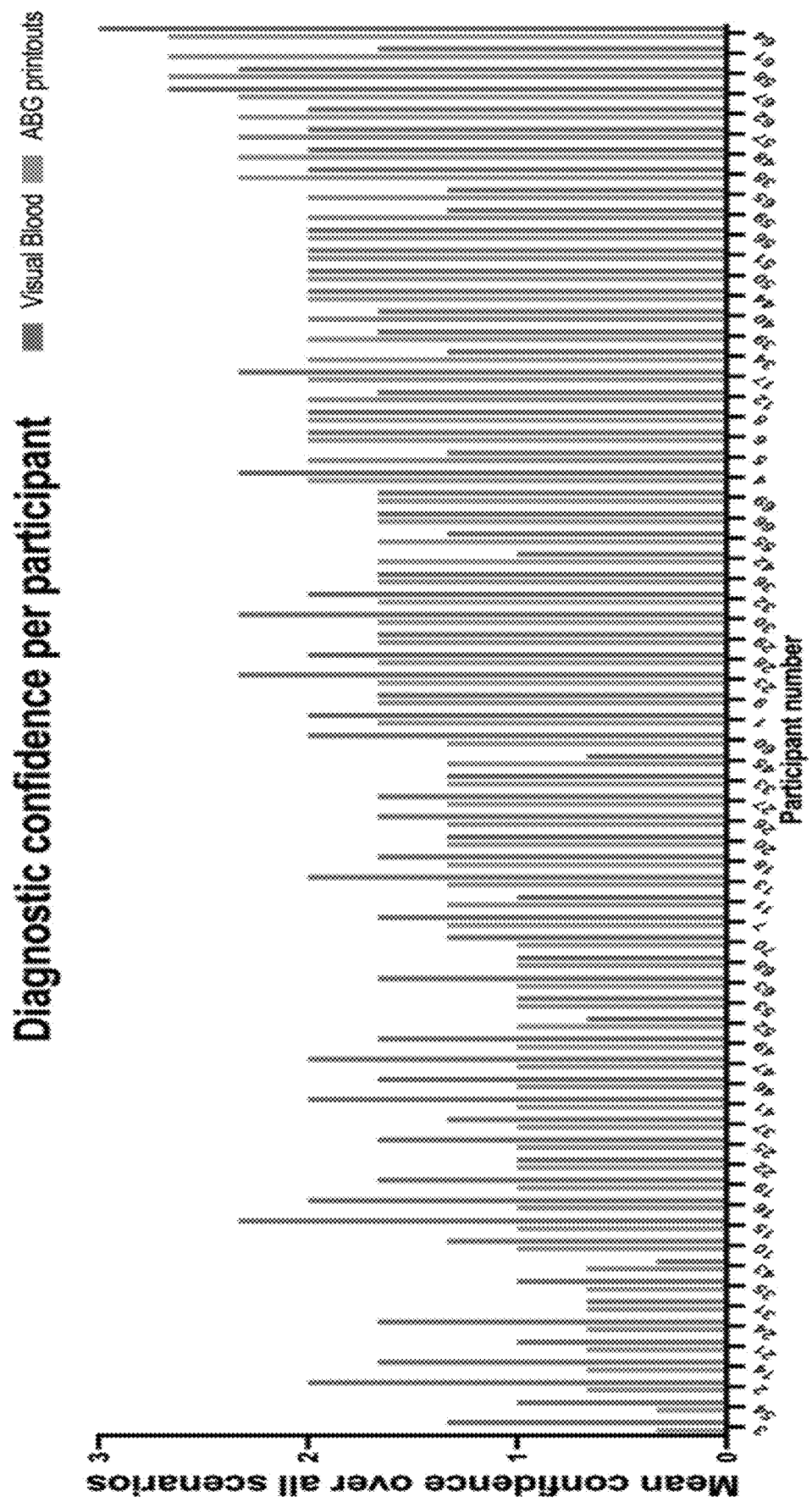
Figure 16:
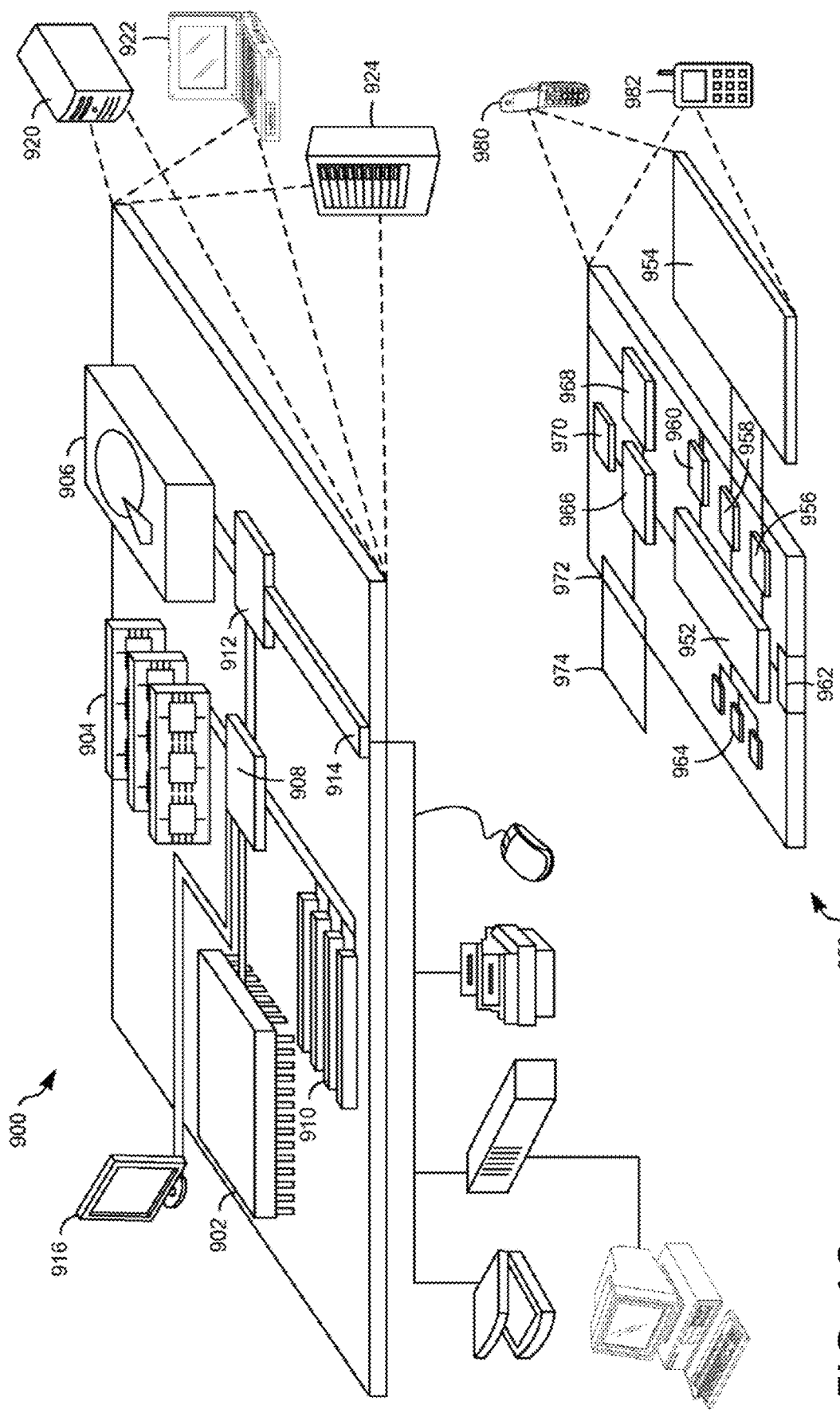
FIG. 16 is a diagram that shows an example of a generic computer device and a generic mobile computer device, which may be used with the techniques described here.

In part two, AGR was compared with conventional ABG result printouts. FIGS. 14A, 14B show the regression model results. FIGS. 15A to 15C show the study results on an individual participant level. In FIGS. 15A to 15C, for each study participant the results achieved when using AGR (the dark grey bars labeled "Visual Blood") are compared with the results achieved when using classic ABG printouts (light grey bars). For each patient, in the respective pair of bars the dark grey AGR related bar is on the right and the light grey ABG related bar is on the left side.

Clinical Diagnoses

Regarding the primary outcome, the correct diagnosis was made 180/210 (86%) times using AGR compared to 142/210 (68%) times using the conventional ABG result printouts. The mixed logistic regression model showed an odds ratio (OR) of 3.4 (95% CI 2.00-5.79, p<0.001) in favor of AGR as illustrated in FIG. 14A (in FIGS. 14* and 15*, AGR is referred to as "Visual Blood").

Parameter Perception

When participants used AGR, more parameters were correctly perceived (3293/3780, 87%) versus conventional ABG result printouts (2915/3780, 77%). The mixed logistic regression model showed more than twice the odds (OR 2.16, 95% CI 1.90-2.46, p<0.001) that participants perceived parameters correctly when they used AGR instead of conventional ABG result printouts as illustrated in FIG. 14A.

The mixed linear model showed that participants with lower performance with conventional ABG printouts benefited most from AGR. The difference in the number of correctly recognized parameters using conventional ABG result versus AGR increased by one point for every point that the conventional ABG diagnostic performance was lower (coefficient 0.96, 95% CI −0.80 to −1.04).

Diagnostic Confidence

The mixed logistic regression model for assessing perceived diagnostic confidence (cf. FIG. 14A) showed that it was higher when participants used AGR versus conventional ABG result printouts (OR 1.88, 95% CI 1.67-2.11, p<0.001).

Perceived Workload

The linear mixed model for assessing perceived workload (cf. FIG. 14B) showed that it was lower when participants used VB versus conventional ABG result printouts (coefficient −3.2, 95% CI −3.77 to −2.64).

Discussion

This multimodal study investigated AGR, a technology visualizing ABG results developed to improve caregivers' situation awareness in ABG interpretation. The study found that AGR enabled participants correctly diagnose more ABG cases, with a higher perceived diagnostic confidence and a reduced perceived workload compared to a conventional ABG result printout. Furthermore, the participants could easily learn to recognize the visualizations from a short educational video and rated their experience positively.

The substantial effect sizes observed to date with these technologies demonstrates their significant potential to improve decision-making.

In this study, we also found that AGR improved perceived diagnostic confidence, was easy to learn and was most helpful to participants who had fewer correct diagnoses with the conventional ABG result printout and who were younger. These results suggest that AGR helps to shorten new caregivers' education times and enables all members of a care team to participate in clinical decision-making. This aspect is particularly important as projections from the World Health Organization are for ever-increasing patient numbers, case complexity, and a global shortage of healthcare professionals.

The underlying mechanism for the improvements found with AGR appears to be in its situational awareness-oriented design. For example, for the AGR study, a high number of lumps of sugar flowing through the artery indicated a high blood glucose level. This representation reduces caregivers' cognitive effort, as the translation and classification of text abbreviations and associated numbers and their integration into caregivers' own mental model are no longer necessary. Streamlining this mental model creation process also results in the improved confidence and reduced perceived workload observed with AGR. Pooled analyses found that task performance was proportional to perceived diagnostic confidence and inversely proportional to workload. Justified diagnostic confidence is vital because clinicians who feel justifiably confident can make better and faster decisions. They do not need to second-guess and can react quickly and decisively.

AGR is designed to leave the final diagnosis to the human decision-makers. The caregivers are provided with visualizations to efficiently present the information but not to make a definitive diagnosis for them, as would be the case with a text output of the diagnosis. So AGR is used as a support tool for the caregivers supporting them in making fast and correct diagnosis decisions.

A recent study has shown that visualizations that have a logical relation to reality can be recognized even without an instructional video. This quality is desirable because there is often little time to obtain explanations in real life.

Conclusions

In this study, AGR enabled caregivers to correctly interpret more ABG results with little prior training and increased their perceived diagnostic confidence. The study adds to the growing body of research showing that decision-support tools developed around our human abilities can streamline caregivers' decision-making and help providers reach their full potential.

FIG. 14 is a diagram that shows an example of a generic computer device 900 and a generic mobile computer device 950, which may be used with the techniques described here. Computing device 900 is intended to represent various forms of digital computers, such as laptops, desktops, workstations, personal digital assistants, servers, blade servers, mainframes, and other appropriate computers. Generic computer device 900 may correspond to the computer system 100 of FIG. 1 for efficient index creation and enhanced real-time patient monitoring. Computing device 950 is intended to represent various forms of mobile devices, such as personal digital assistants, cellular telephones, smart phones, and other similar computing devices. For example, computing device 950 may be used as a frontend by a user (e.g., medically trained staff) to interact with the computing device 900. For example, the user may receive real-time monitoring data (e.g., an alarm) about the health state of a particular intensive care patient while treating another patient. The user can then immediately shift the focus of attention to that particular patient. The components shown here, their connections and relationships, and their functions, are meant to be exemplary only, and are not meant to limit implementations of the descriptions described and/or claimed in this document.

Computing device 900 includes a processor 902, memory 904, a storage device 906, a high-speed interface 908 connecting to memory 904 and high-speed expansion ports 910, and a low speed interface 912 connecting to low speed bus 914 and storage device 906. Each of the components 902, 904, 906, 908, 910, and 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high speed interface 908. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 904, the storage device 906, or memory on processor 902.

The high-speed controller 908 manages bandwidth-intensive operations for the computing device 900, while the low speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a Microdrive or other device, to provide additional storage. Each of the components 950, 952, 964, 954, 966, and 968, are interconnected using various buses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provide in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 984 may also be provided and connected to device 950 through expansion interface 982, which may include, for example, a SIMM (Single In Line Memory Module) card interface. Such expansion memory 984 may provide extra storage space for device 950, or may also store applications or other information for device 950. Specifically, expansion memory 984 may include instructions to carry out or supplement the processes described above, and may include secure information also. Thus, for example, expansion memory 984 may act as a security module for device 950, and may be programmed with instructions that permit secure use of device 950. In addition, secure applications may be provided via the SIMM cards, along with additional information, such as placing the identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 984, or memory on processor 952 that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, WiFi, or other such transceiver (not shown). In addition, GPS (Global Positioning System) receiver module 980 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smart phone 982, personal digital assistant, or another similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing device that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing device can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the description.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

The invention claimed is:

1. A computer-implemented method for rendering representations of blood gas state parameters of a patient to support a medically trained person in blood gas analysis of the patient's blood, comprising:
receiving, from a data source, time series of sampled measurement values obtained from a plurality of blood gas analysis sensors for the following blood gas state parameters of the patient: Glucose, Chloride, Potassium, Calcium, Sodium, and Hemoglobin;
mapping each state parameter to a predefined corresponding graphical representation with each graphical representation for a particular state parameter being distinct from all graphical representations of remaining state parameters; and
rendering, in a virtual 3D tunnel shaped scene representing an inside of an artery, animated visualizations of the graphical representations, in accordance with predefined animation rules, such that respective graphical objects move through the inside of the artery and reflect current values of the respective state parameters, wherein the predefined animation rules comprise:
for the Glucose state parameter:
a non-blinking single Glucose object indicating normal Glucose concentration,
a blinking Glucose object indicating a too low Glucose concentration, and
a cluster of a plurality of non-blinking Glucose objects indicating a too high Glucose concentration;
for electrolyte state parameters Chloride, Potassium, Calcium, and Sodium:
a two-by-two arrangement of four electrolyte objects with a single non-blinking electrolyte object for each electrolyte indicating normal concentration of the electrolyte parameters,
the two-by-two arrangement wherein a blinking electrolyte object indicating a too low concentration of the respective electrolyte parameter, and
the two-by-two arrangement wherein a replication of a particular non-blinking electrolyte object around the two-by-two arrangement indicating a too high concentration of the respective electrolyte parameter; and
for the Hemoglobin state parameter:
a non-blinking single red blood cell object indicating a normal Hemoglobin value,
a blinking single red blood cell object indicating a too low Hemoglobin value as an indicator for anemia, and
a cluster of a plurality of non-blinking red blood cell objects indicating a too high Hemoglobin value.

2. The method of claim 1, wherein all blinking objects have two alternating states comprising a solid object visualization state and a non-solid object state, a blinking object in the non-solid object state being outlined with dashed lines.

3. The method of claim 1, wherein:
the cluster of the plurality of non-blinking red blood cell objects is rendered such that the plurality of non-blinking red blood cell objects is placed inside a virtual geometric body with predefined blood cell cluster specific dimensions;
the cluster of the plurality of non-blinking Glucose objects is rendered such that the plurality of non-blinking Glucose objects is placed inside a virtual geometric body with predefined Glucose cluster specific dimensions; and
the replication of the particular non-blinking electrolyte object around the two-by-two arrangement is rendered such that the particular non-blinking electrolyte object in the two-by-two arrangement defines the center of a virtual geometric body with predefined electrolyte specific dimensions and one or more replications of the particular non-blinking electrolyte object are rendered within the virtual geometric body with the predefined electrolyte specific dimensions.

4. The method of claim 1, further comprising:
receiving, from the data source, further time series of sampled anion gap state parameter values associated with unspecific anions;
mapping the anion gap state parameter to a predefined corresponding graphical anion gap representation being distinct from all graphical representations of the remaining state parameters; and
rendering the anion gap representation in relation to the two-by-two arrangement for the electrolyte state parameters in accordance with predefined anion gap animation rules comprising:
the two-by-two arrangement for the electrolyte state parameters being orbited by an unspecific anion object, indicating a normal anion gap, with the center of the orbit located at the center of the two-by-two arrangement, and a radius of the orbit being greater than a predefined electrolyte radius used for rendering replications of a particular non-blinking electrolyte object around the two-by-two arrangement,
the two-by-two arrangement for the electrolyte state parameters being orbited with said radius of the orbit by a plurality of unspecific anion objects, indicating a too high anion gap, and
the two-by-two arrangement for the electrolyte state parameters being orbited by a single blinking unspecific anion object, indicating a too low anion gap.

5. The method of claim 1, further comprising:
receiving, from the data source, further time series of sampled measurement values for an oxygen affinity state parameter of the patient;
mapping the oxygen affinity state parameter to a predefined corresponding graphical oxygen affinity representation being distinct from all graphical representations of the remaining state parameters; and
rendering the oxygen affinity representation in relation to the red blood cell object, with a plurality of bound oxygen objects attached to the red blood cell object, in accordance with predefined oxygen affinity animation rules comprising:
one oxygen object being released by the red blood cell object in the course of moving through the artery indicating normal oxygen affinity,
all oxygen objects being released by a red blood cell object in the course of moving through the artery indicating too low oxygen affinity, and
all oxygen objects with a rubber band animation oscillating between their neutral positions and a position at a predefined oscillation distance from a red blood cell surface, in the course of moving through the artery, indicating too high oxygen affinity.

6. The method of claim 1, further comprising:
receiving, from the data source, further time series of sampled measurement values for an oxygen saturation state parameter of the patient;
mapping the oxygen saturation state parameter to a predefined corresponding graphical oxygen saturation representation being distinct from all graphical representations of the remaining state parameters; and
rendering the oxygen saturation representation in accordance with predefined oxygen saturation animation rules comprising:
a non-blinking single red blood cell object loaded with a plurality of bound oxygen objects, indicating a normal oxygen saturation, and
a non-blinking single red blood cell object having an alert color with a single bound oxygen object, indicating a too low oxygen saturation.

7. The method of claim 6, further comprising:
receiving, from the data source, further time series of sampled measurement values for a Methemoglobin state parameter of the patient;
mapping the Methemoglobin state parameter to a predefined corresponding graphical Methemoglobin representation being distinct from all graphical representations of the remaining state parameters; and
rendering the Methemoglobin representation in accordance with predefined Methemoglobin animation rules comprising:
the non-blinking single red blood cell object loaded with a plurality of bound oxygen objects, indicating a normal Methemoglobin level, and
the non-blinking single red blood cell object having the alert color with a single bound oxygen object and, in addition, a plurality of Methemoglobin level labels, indicating a too high Methemoglobin level with limited oxygen transport capacity.

8. The method of claim 1, further comprising:
receiving, from the data source, further time series of sampled measurement values for a Carbonmonoxy state parameter of the patient;
mapping the Carbonmonoxy state parameter to a predefined corresponding graphical Carbonmonoxy representation being distinct from all graphical representations of the remaining state parameters; and
rendering the Carbonmonoxy representation in accordance with predefined Carbonmonoxy animation rules comprising:
a non-blinking single red blood cell object loaded with a plurality of bound oxygen objects, indicating a normal Carbonmonoxy level, and
a single red blood cell object having an alert color with a plurality of bound carbonmonoxy objects instead of the bound oxygen objects, and with the red blood cell leaving behind a trail of fire in the course of moving through the artery, indicating a too high Carbonmonoxy level.

9. The method of claim 1, further comprising:
receiving, from the data source, further time series of sampled measurement values for an Oxygen Partial Pressure (OPP) state parameter of the patient;
mapping the OPP state parameter to a predefined corresponding graphical OPP representation being distinct from all graphical representations of the remaining state parameters; and
rendering the OPP representation in accordance with predefined OPP animation rules comprising:
a non-blinking single red blood cell object indicating a normal OPP level,
a non-blinking single red blood cell object surrounded by a cluster with at least a predefined high-OPP-level-number of unbound non-blinking oxygen objects, indicating a high OPP level, and
a non-blinking single red blood cell object surrounded by a cluster with at most a predefined low-OPP-level-number of unbound blinking oxygen objects, indicating a low OPP level.

10. The method of claim 1, further comprising:
receiving, from the data source, further time series of sampled measurement values for a CO2 partial pressure state parameter of the patient;
mapping the CO2 partial pressure state parameter to a predefined corresponding graphical CO2 partial pressure representation being distinct from all graphical representations of the remaining state parameters; and
rendering the CO2 partial pressure representation in accordance with predefined CO2 partial pressure animation rules such that respective graphical CO2 objects move through the inside of the artery and reflect current values of the CO2 partial pressure state parameter comprising:
a non-blinking single CO2 object indicating a normal CO2 partial pressure,
a blinking single CO2 object indicating a too low CO2 partial pressure, and
a cluster of a plurality of non-blinking CO2 objects indicating a too high CO2 partial pressure.

11. The method of claim 1, further comprising:
receiving, from the data source, further time series of sampled measurement values for a Plasma Osmolarity state parameter of the patient,
mapping the Plasma Osmolarity state parameter to a predefined corresponding graphical Plasma Osmolarity representation being distinct from all graphical representations of the remaining state parameters; and
rendering, in the virtual 3D tunnel shaped scene representing the inside of the artery, animated visualizations of graphical Plasma Osmolarity representations, in accordance with predefined Plasma Osmolarity animation rules comprising:
a plurality of droplet objects diffusing in and out through a blood vessel wall of the artery, indicating normal Plasma Osmolarity, wherein each droplet object has a shape indicating a diffusion direction of the respective droplet object,
a plurality of droplet objects only diffusing into the artery through the blood vessel wall, indicating a too low Plasma Osmolarity, and
a plurality of droplet objects only diffusing out of the artery through the blood vessel wall, indicating a too high Plasma Osmolarity.

12. The method of claim 1, further comprising:
receiving, from the data source, further time series of sampled measurement values for Acid-Base Balance state parameters of the patient, comprising pH level, bicarbonate concentration, base excess level, lactate concentration,
mapping each Acid-Base Balance state parameter to a predefined corresponding graphical Acid-Base Balance representation being distinct from all graphical representations of the remaining state parameters; and rendering, in the virtual 3D tunnel shaped scene representing the inside of the artery, animated visualizations of the graphical Acid-Base Balance representations by using an animated balance object placed at a fixed location at a bottom of the artery, in accordance with predefined Acid-Base Balance animation rules, the Acid-Base Balance animation rules comprising:

for the pH level state parameter:
  a non-blinking single H⁺ object associated with an acid weighing pan of the balance object, and a non-blinking unspecific base object associated with a base weighing pan of the balance object, with both weighing pans being balanced, indicating a normal pH level,
  a cluster of a plurality of non-blinking H⁺ objects associated with the acid weighing pan wherein the acid weighing pan is down, indicating a too low pH level, and
  a blinking H⁺ object associated with the acid weighing pan wherein the base weighing pan is down, indicating a too high pH level with alkaline components predominating;

for the base excess level state parameter:
  a cluster of a plurality of non-blinking unspecific base objects associated with the base weighing pan continuously releasing soap bubbles indicating too high base excess, and
  a blinking single unspecific base object associated with the base weighing pan indicating too low base excess;

for the lactate concentration state parameter:
  a cluster of a plurality of non-blinking milk bottle objects associated with the acid weighing pan, indicating a too high value of lactate concentration, and
  any other balance representation indicating a normal lactate concentration;

for the bicarbonate concentration state parameter:
  a non-blinking single HCO₃— object associated with the base weighing pan, indicating normal bicarbonate concentration,
  a blinking single HCO₃— object associated with the base weighing pan, indicating too low bicarbonate concentration, and
  a cluster of a plurality of non-blinking HCO₃— objects associated with the base weighing pan, indicating a too high bicarbonate concentration.

13. A computer readable medium comprising program instructions that, when loaded into a memory of a computing device and executed by at least one processor of the computing device, cause the at least one processor to execute the following steps for rendering representations of blood gas state parameters of a patient to support a medically trained person in blood gas analysis of the patient's blood:
  receiving, from a data source, time series of sampled measurement values obtained from a plurality of blood gas analysis sensors for the following blood gas state parameters of the patient: Glucose, Chloride, Potassium, Calcium, Sodium, and Hemoglobin;
  mapping each state parameter to a predefined corresponding graphical representation with each graphical representation for a particular state parameter being distinct from all graphical representations of remaining state parameters; and
  rendering, in a virtual 3D tunnel shaped scene representing an inside of an artery, animated visualizations of the graphical representations, in accordance with predefined animation rules, such that respective graphical objects move through the inside of the artery and reflect current values of the respective state parameters, wherein the predefined animation rules comprise:

for the Glucose state parameter:
  a non-blinking single Glucose object indicating normal Glucose concentration,
  a blinking Glucose object indicating a too low Glucose concentration, and
  a cluster of a plurality of non-blinking Glucose objects indicating a too high Glucose concentration;

for electrolyte state parameters Chloride, Potassium, Calcium, and Sodium:
  a two-by-two arrangement of four electrolyte objects with a single non-blinking electrolyte object for each electrolyte indicating normal concentration of the electrolyte parameters,
  the two-by-two arrangement wherein a blinking electrolyte object indicating a too low concentration of the respective electrolyte parameter, and
  the two-by-two arrangement wherein a replication of a particular non-blinking electrolyte object around the two-by-two arrangement indicating a too high concentration of the respective electrolyte parameter; and for the Hemoglobin state parameter:
  a non-blinking single red blood cell object indicating a normal Hemoglobin value,
  a blinking single red blood cell object indicating a too low Hemoglobin value as an indicator for anemia, and
  a cluster of a plurality of non-blinking red blood cell objects indicating a too high Hemoglobin value.

14. The computer readable medium of claim 13, wherein all blinking objects have two alternating states comprising a solid object visualization state and a non-solid object state, a blinking object in the non-solid object state being outlined with dashed lines.

15. The computer readable medium of claim 13, wherein:
  the cluster of the plurality of non-blinking red blood cell objects is rendered such that the plurality of non-blinking red blood cell objects is placed inside a virtual geometric body with predefined blood cell cluster specific dimensions;
  the cluster of the plurality of non-blinking Glucose objects is rendered such that the plurality of non-blinking Glucose objects is placed inside a virtual geometric body with predefined Glucose cluster specific dimensions; and
  the replication of the particular non-blinking electrolyte object around the two-by-two arrangement is rendered such that the particular non-blinking electrolyte object in the two-by-two arrangement defines the center of a virtual geometric body with predefined electrolyte specific dimensions and one or more replications of the particular non-blinking electrolyte object are rendered within the virtual geometric body with the predefined electrolyte specific dimensions.

16. A computer system for rendering representations of medical state parameters of a patient to support a medically trained person in blood gas analysis of the blood of the patient, comprising:
  an interface adapted to receive, from a data source, time series of sampled measurement values obtained from a plurality of blood gas analysis sensors for the following blood gas state parameters of the patient: Glucose, Chloride, Potassium, Calcium, Sodium, and Hemoglobin;

a mapper module adapted to map each state parameter to a predefined corresponding graphical representation with each graphical representation for a particular state parameter being distinct from all graphical representations of a remaining state parameters; and a renderer module adapted to render, in a virtual 3D tunnel shaped scene representing an inside of an artery, animated visualizations of the graphical representations, in accordance with predefined animation rules, such that respective graphical objects move through the inside of the artery and reflect current values of the respective state parameters, wherein the predefined animation rules comprise:

for the Glucose state parameter:
　a non-blinking single Glucose object indicating normal Glucose concentration,
　a blinking Glucose object indicating a too low Glucose concentration, and
　a cluster of a plurality of non-blinking Glucose objects indicating a too high Glucose concentration;

for electrolyte state parameters Chloride, Potassium, Calcium, and Sodium:
　a two-by-two arrangement of four electrolyte objects with a single non-blinking electrolyte object for each electrolyte indicating normal concentration of the electrolyte parameters,
　the two-by-two arrangement wherein a blinking electrolyte object indicating a too low concentration of the respective electrolyte parameter, and
　the two-by-two arrangement wherein a replication of a particular non-blinking electrolyte object around the two-by-two arrangement indicating a too high concentration of the respective electrolyte parameter; and for the Hemoglobin state parameter:
　a non-blinking single red blood cell object indicating a normal Hemoglobin value,
　a blinking single red blood cell object indicating a too low Hemoglobin value as an indicator for anemia, and
　a cluster of a plurality of non-blinking red blood cell objects indicating a too high Hemoglobin value.

17. The computer system of claim 16, wherein all blinking objects have two alternating states comprising a solid object visualization state and a non-solid object state, a blinking object in the non-solid object state being outlined with dashed lines.

18. The computer system of claim 16, wherein:
the cluster of the plurality of non-blinking red blood cell objects is rendered such that the plurality of non-blinking red blood cell objects is placed inside a virtual geometric body with predefined blood cell cluster specific dimensions;
the cluster of the plurality of non-blinking Glucose objects is rendered such that the plurality of non-blinking Glucose objects is placed inside a virtual geometric body with predefined Glucose cluster specific dimensions; and
the replication of the particular non-blinking electrolyte object around the two-by-two arrangement is rendered such that the particular non-blinking electrolyte object in the two-by-two arrangement defines the center of a virtual geometric body with predefined electrolyte specific dimensions and one or more replications of the particular non-blinking electrolyte object are rendered within the virtual geometric body with the predefined electrolyte specific dimensions.

19. The system of claim 16, wherein:
the interface is further adapted to receive, from the data source, further time series of sampled measurement values for a Plasma Osmolarity state parameter of the patient,
the mapper module is further adapted to map the Plasma Osmolarity state parameter to a predefined corresponding graphical Plasma Osmolarity representation being distinct from all graphical representations of the remaining state parameters; and
the renderer module is further adapted to render, in the virtual 3D tunnel shaped scene representing the inside of the artery, animated visualizations of graphical Plasma Osmolarity representations, in accordance with predefined Plasma Osmolarity animation rules comprising:
　a plurality of droplet objects diffusing in and out through a blood vessel wall of the artery, indicating normal Plasma Osmolarity, wherein each droplet object has a shape indicating a diffusion direction of the respective droplet object,
　a plurality of droplet objects only diffusing into the artery through the blood vessel wall, indicating a too low Plasma Osmolarity, and
　a plurality of droplet objects only diffusing out of the artery through the blood vessel wall, indicating a too high Plasma Osmolarity.

20. The system of claim 16, wherein:
the interface is further adapted to receive, from the data source, further time series of sampled measurement values for Acid-Base Balance state parameters of the patient, comprising pH level, bicarbonate concentration, base excess level, lactate concentration,
the mapper module is further adapted to map each Acid-Base Balance state parameter to a predefined corresponding graphical Acid-Base Balance representation being distinct from all graphical representations of the remaining state parameters; and
the renderer module is further adapted to render, in the virtual 3D tunnel shaped scene representing the inside of the artery, animated visualizations of the graphical Acid-Base Balance representations by using an animated balance object placed at a fixed location at a bottom of the artery, in accordance with predefined Acid-Base Balance animation rules, the Acid-Base Balance animation rules comprising:
for the pH level state parameter:
　a non-blinking single $H^+$ object associated with an acid weighing pan of the balance object, and a non-blinking unspecific base object associated with a base weighing pan of the balance object, with both weighing pans being balanced, indicating a normal pH level,
　a cluster of a plurality of non-blinking $H^+$ objects associated with the acid weighing pan wherein the acid weighing pan is down, indicating a too low pH level, and
　a blinking $H^+$ object associated with the acid weighing pan wherein the base weighing pan is down, indicating a too high pH level with alkaline components predominating;
for the base excess level state parameter:
　a cluster of a plurality of non-blinking unspecific base objects associated with the base weighing pan continuously releasing soap bubbles indicating too high base excess, and a blinking single unspecific base object associated with the base weighing pan indicating too low base excess;

for the lactate concentration state parameter:
a cluster of a plurality of non-blinking milk bottle objects associated with the acid weighing pan, indicating a too high value of lactate concentration, and
any other balance representation indicating a normal lactate concentration;

for the bicarbonate concentration state parameter:
a non-blinking single $HCO_3-$ object associated with the base weighing, indicating normal bicarbonate concentration,
a blinking single $HCO_3-$ object associated with the base weighing pan, indicating too low bicarbonate concentration, and
a cluster of a plurality of non-blinking $HCO_3-$ objects associated with the base weighing pan, indicating a too high bicarbonate concentration.

\* \* \* \* \*